United States Patent
Lorbert et al.

(10) Patent No.: US 6,342,651 B1
(45) Date of Patent: Jan. 29, 2002

(54) REDUCTIVE COMBUSTION OF AMMONIUM SALTS OF SULFURIC ACID

(75) Inventors: Stephen J. Lorbert, St. Louis; James M. Willock, Ballwin; Lewis B. Irvine, Chesterfield; Shubhender Kapila, Rolla; Virgil J. Flanigan, Rolla; Paul K. S. Nam, Rolla; Yvonne M. Liske, Rolla, all of MO (US)

(73) Assignee: Novus International, Inc., St. Louis, MO (US)

( * ) Notice: Subject to any disclaimer, the term of this patent is extended or adjusted under 35 U.S.C. 154(b) by 0 days.

(21) Appl. No.: 09/632,999

(22) Filed: Aug. 4, 2000

Related U.S. Application Data
(60) Provisional application No. 60/147,751, filed on Aug. 5, 1999.

(51) Int. Cl.[7] .................................................. C01B 17/00
(52) U.S. Cl. ...................... 588/238; 588/244; 423/220; 423/244.09; 423/523; 423/563; 423/564; 423/443
(58) Field of Search ................................. 588/238, 244; 423/220, 244.09, 523, 545, 563, 564, 443

(56) References Cited

U.S. PATENT DOCUMENTS

| | | | |
|---|---|---|---|
| 3,047,369 A | 7/1962 | Montgomery | 23/252 |
| 3,243,261 A | 3/1966 | Deiters | 23/174 |

(List continued on next page.)

FOREIGN PATENT DOCUMENTS

| | | |
|---|---|---|
| DE | 4 101 497 A1 | 7/1992 |
| DE | 19754562 A1 | 6/1999 |
| EP | 0 091 679 B1 | 1/1986 |
| EP | 0 244 206 A2 | 11/1987 |
| EP | 0 421 629 A1 | 4/1991 |
| EP | 0 496 101 A1 | 7/1992 |
| EP | 0 516 001 A1 | 12/1992 |
| EP | 0 850 922 A1 | 12/1997 |
| FR | 72.04117 | 9/1972 |
| FR | 2 252 980 | 6/1975 |
| GB | 1033325 | 7/1964 |
| GB | 1029748 | 3/1965 |

OTHER PUBLICATIONS

Abstract for Japanese Patent Pub. No. 63201005, Published Aug. 19, 1988.
PCT International Search Report for International Application No. PCT US 00/21493 (4 pages), Nov. 24, 2000.
White & White, "Manufacture of Sodium Sulfide", Ind. Eng. Chem, 28(1) pp. 244–246 (1936).
Nyman and O'Brien, Catalytic Reduction of Sodium Sulfate, Ind. Eng. Chem., 39(8) pp. 1021–1023 (1947).
Berk, et al., "Hydrogen Reduction of Alkali Sulfate", Ind. Eng. Chem. Proc. Des. Dev., 10(1) pp. 7–13 (1971).
Diaz–Bossio, et al., "Reductive Decomposition of Calcium Sulfate Utilizing Carbon Monoxide and Hydrogen", Chem. Eng. Sci., Ud. 40, No. 3 pp. 319–324 (1985).

(List continued on next page.)

*Primary Examiner*—Steven P. Griffin
*Assistant Examiner*—Timothy C. Vandy
(74) *Attorney, Agent, or Firm*—Senniger, Powers, Leavitt & Roedel

(57) ABSTRACT

A process is provided for the combustion of ammonium salts of sulfuric acid contained in aqueous media. More particularly, a reductive combustion process which produces a combustion gas containing a divalent sulfur compound having a high concentration of hydrogen sulfide. The process is suitable for combusting ammonium salts of sulfuric acid produced during manufacture of 2-hydroxy-4-methylthiobutanoic acid (HMBA) or methionine. The divalent sulfur compounds in the combustion gas may be further converted to other useful sulfur products and recycled for use in the manufacture of HMBA or methionine.

42 Claims, 10 Drawing Sheets

U.S. PATENT DOCUMENTS

| | | | |
|---|---|---|---|
| 3,282,646 A | 11/1966 | Bonfield et al. | 23/177 |
| 3,383,170 A | 5/1968 | Furkert et al. | 23/177 |
| 3,549,320 A | 12/1970 | Isbell, Jr. et al. | 23/168 |
| 3,590,555 A | 7/1971 | Wackernagel | 55/51 |
| 3,674,427 A | 7/1972 | Welty, Jr. | 23/119 |
| 3,726,957 A | 4/1973 | Lind | 423/170 |
| 3,767,777 A | 10/1973 | Frye et al. | 423/575 |
| 3,929,977 A | 12/1975 | Brennan | 423/520 |
| 3,954,955 A | 5/1976 | Furkert | 423/541 |
| 4,120,944 A | 10/1978 | Kubicek | 423/416 |
| 4,208,390 A | 6/1980 | Hirabayashi et al. | 423/356 |
| 4,302,434 A | 11/1981 | Hellmer et al. | 423/573 |
| 4,311,683 A | 1/1982 | Hass et al. | 423/573 |
| 4,410,731 A | 10/1983 | Buchholz | 568/70 |
| 4,449,006 A | 5/1984 | Haines | 568/70 |
| 4,490,347 A | 12/1984 | Gelblum | 423/521 |
| 4,520,020 A | 5/1985 | Loebenstein et al. | 424/197.1 |
| 4,524,077 A | 6/1985 | Ruest et al. | 514/557 |
| 4,530,704 A | 7/1985 | Jones et al. | 55/48 |
| 4,544,649 A | 10/1985 | Wachs et al. | 502/350 |
| 4,570,020 A | 2/1986 | Ratcliffe et al. | 568/70 |
| 4,665,242 A | 5/1987 | Boulinguiez et al. | 568/70 |
| 4,668,825 A | 5/1987 | Ratcliffe et al. | 568/70 |
| 4,912,257 A | 3/1990 | Hernandez et al. | 562/581 |
| 5,304,361 A | 4/1994 | Parisi | 423/220 |
| 5,352,837 A | 10/1994 | Hsu et al. | 568/41 |
| 5,399,323 A | 3/1995 | Paisley et al. | 423/170 |
| 5,498,790 A | 3/1996 | Grendel et al. | 562/581 |
| 5,637,766 A | 6/1997 | Hsu et al. | 562/512 |
| 5,663,409 A | 9/1997 | Blackburn et al. | 558/351 |
| 5,670,128 A | 9/1997 | Grendel et al. | 423/531 |
| 5,705,675 A | 1/1998 | Blackburn et al. | 558/351 |
| 5,744,647 A | 4/1998 | Hsu et al. | 568/41 |
| 5,851,265 A | 12/1998 | Burmaster et al. | 95/159 |
| 5,856,567 A | 1/1999 | Hsu et al. | 562/581 |
| 5,866,721 A | 2/1999 | Hofen et al. | 568/71 |
| 5,874,630 A | 2/1999 | Cook et al. | 568/71 |
| 5,905,171 A | 5/1999 | Hsu | 568/41 |
| 5,910,611 A | 6/1999 | Gregory, Jr. et al. | 564/497 |
| 6,017,507 A | 1/2000 | Nougayrede et al. | 423/573.1 |
| 6,024,933 A | 2/2000 | Legendre et al. | 423/567.1 |

OTHER PUBLICATIONS

Sarlis and Berk, "Reduction of Sulfur Dioxide with Methane over Activated Alumina", Ind. Eng. Chem. Res., vol. 27, pp. 1951–1954 (1988).

Li and van Heinigen, "Kinetics of Sodium Sulfate Reduction in the Solid State by Carbon Monoxide," Chem. Eng. Sci., 43(8) pp. 2079–2085 (1988).

Mulligan and Berk, "Reduction of Sulfur Dioxide with Methane over Selected Transition Metal Sulfides," Ind. Eng. Chem. Res., vol. 28 pp. 926–931 (1989).

Pacewska and Pysiak, "Thermal Decomposition of Basic Aluminum–Ammonium Sulfate (BAAS) in Hydrogen Atmosphere," J. Therm. Anal., vol. 37, pp. 1665–1672 (1991).

Ng, et al., "Carbonation Conversion of Aqueous Sodium Sulfide to Hydrogen Sulfide," Environ. Sci. Tech., vol. 27, pp. 2158–2161 (1993).

Zou, et al., "Carbon Monoxide Reduction of Sodium Sulfate Mixed with Sodium Titanate," Can. J. Chem. Eng., vol. 71, pp. 892–900 (1993).

Gowdy, et al., "VOP's Selectox™ Process, Improvements in the Technology," Presented at the 48th annual Lawrence Reid Gas Conditioning Conference, Mar. 1–4, 1998, Norman, Oklahoma.

PCT WO 98/47813, publication date Oct. 29, 1998.
PCT WO 99/33748, publication date Jul. 8, 1999.
PCT WO 99/33778, publication date Jul. 8, 1999.

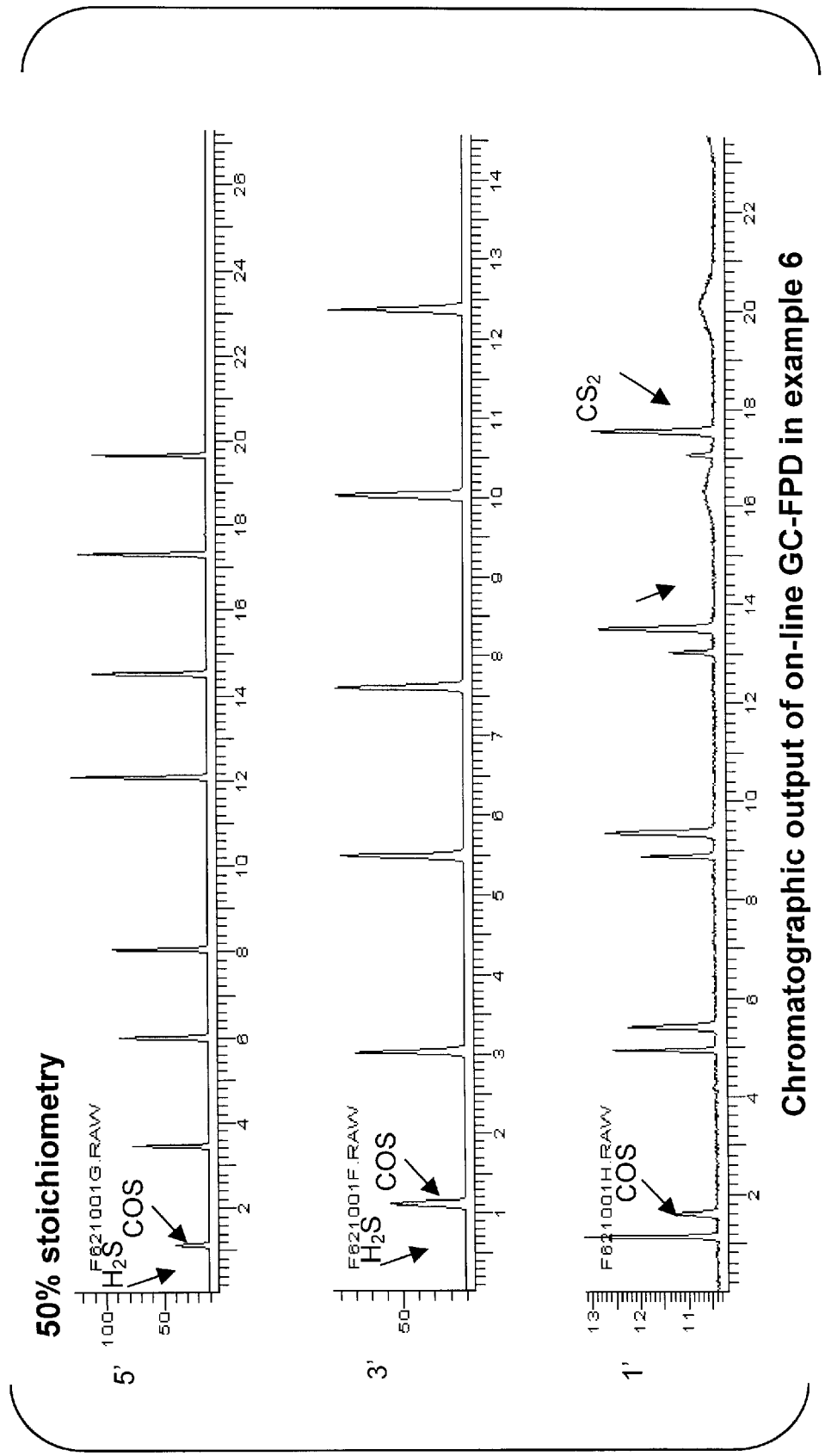

REDUCTIVE COMBUSTION OF AMMONIUM SALTS OF SULFURIC ACID

This application claims the benefit of U.S. provisional application Ser. No. 60/147,751 filed Aug. 5, 1999, the disclosure of which is expressly incorporated herein by reference.

BACKGROUND OF THE INVENTION

This invention relates to the oxidation of ammonium salts of sulfuric acid contained in aqueous media; and, more particularly, to a reductive combustion process which produces a combustion gas containing a divalent sulfur compound such as hydrogen sulfide and/or carbonyl sulfide, and further to the conversion of such divalent sulfur compound to other useful sulfur products.

Various industrial processes produce aqueous by-product streams comprising ammonium salts of sulfuric acid. For example, Ruest U.S. Pat. No. 4,524,077 and Hernandez U.S. Pat. No. 4,912,257 both describe processes for the preparation of 2-hydroxy-4-methylthiobutanoic acid (HMBA) by sulfuric acid hydrolysis of 2-hydroxy-4-methylthiobutanenitrile (HMBN). In each process, an aqueous hydrolyzate is produced comprising HMBA and ammonium bisulfate. In Ruest, the aqueous hydrolyzate is extracted with a substantially water-immiscible solvent for recovery of the product HMBA. Raffinate from the extraction is stripped for recovery of solvent, producing a bottoms fraction which comprises ammonium bisulfate. Depending on hydrolysis conditions, the raffinate stripper bottoms may also contain some ammonium sulfate or free sulfuric acid.

In Hernandez, the hydrolyzate is neutralized with ammonia, causing separation of an organic phase containing HMBA from an aqueous phase containing ammonium sulfate.

The by-product ammonium salt solutions produced in the Ruest and Hernandez process generally lack economic value, and must be disposed of in some manner. U.S. Pat. Nos. 5,498,790 and 5,670,128 describe processes for the regeneration of sulfuric acid from the by-product ammonium salt solutions, and recycle of the regenerated acid for further hydrolysis of HMBN to HMBA. Processes are known for the recovery of ammonium sulfate for use in fertilizers or other applications. However, such processes are complicated, and the market value of ammonium sulfate is generally not sufficient for recovery of the processing costs.

Other processes which produce by-product ammonium salts of sulfuric acid include the preparation of caprolactam and the preparation of methyl methacrylate. Sulfuric acid regeneration processes have been proposed for treating the by-product salt solutions in these instances as well. See, for example, U.S. Pat. Nos. 3,549,320 and 4,490,347 directed to the treatment of waste ammonium sulfate solution produced in the preparation of methyl methacrylate.

In all the sulfuric acid regeneration processes, a solution or slurry of by-product ammonium salt, or solid particulate salt, is introduced together with fuel into a combustion furnace wherein the salt is pyrolyzed to produce a combustion gas comprising sulfur dioxide, carbon dioxide, water vapor, nitrogen, excess oxygen, and typically oxides of nitrogen. Ammonia released from the salt is burned in the process to yield water vapor and nitrogen. After the gas stream has been cooled and cleaned, it is typically passed to a converter in which sulfur dioxide is catalytically converted to sulfur trioxide. Absorption of sulfur trioxide in sulfuric acid yields concentrated sulfuric acid which may be recycled or otherwise used or sold. Because the object of the sulfuric acid regeneration processes is to produce a gas stream containing both $SO_2$ and $O_2$ for further oxidation in the catalytic converter, all these processes introduce at least a slight excess of oxygen, typically in the form of air.

German Offlengungsschrift 197 54 562 A1 describes an alternative process for the recovery of sulfuric acid from sulfur-containing secondary products of a process for the preparation of HMBA. In that process, an aqueous mixture comprising ammonium sulfate or ammonium bisulfate is introduced into a combustion zone and burned to produce a combustion gas containing sulfur dioxide. The cooled combustion gas is contacted with a hydrogen peroxide solution to produce sulfuric acid. The acid produced can be used for the hydrolysis of HMBN to HMBA.

Certain of the known sulfuric acid regeneration processes use two stage combustion as a means to reduce the concentrations of oxides of nitrogen in the combustion gas leaving the combustion operation. Such operation is described, for example, in U.S. Pat. Nos. 5,498,790 and 5,670,128 wherein the first stage is operated with a slight deficiency of air so that nitrites, ammonia, and any amines contained in the sulfate feed solution are oxidized to nitrogen gas and carbon oxides but not to oxides of nitrogen. The partial combustion gas leaving the first stage contains unburned combustibles and carbon monoxide. To fully convert the carbon, hydrogen and sulfur content of combustibles and carbon monoxide to carbon dioxide, water, and $SO_2$, oxidizing conditions are established in the second stage of the combustion by further injection of air. The sum of the air provided to the two stages is preferably sufficient to provide an oxygen content between about 0.5% and about 5% in the gas leaving the combustion chamber.

BASF DE Offenlegungsschrift 41 01 497 describes a process for thermal workup of waste water containing ammonium sulfate by metering the waste water through a nozzle/burner system, consisting of a burner and a centrally located atomization nozzle, into an adiabatic combustion chamber using a supporting fuel and a suitable oxidizing agent, typically air. Two stage combustion is carried out first at reducing, then at oxidizing conditions. In the first stage, aqueous ammonium sulfate is burned reductively to produce hydrogen sulfide in a combustible mixture of reducing gases. Nitrogen bound in the ammonium sulfate is mainly reacted to nitrogen ($N_2$) and not to nitrogen oxides. In the second stage additional air is added to facilitate complete combustion of the reduced species in the offgas, $H_2S$ being converted to $SO_2$. The process is said to be characterized by the fact that with reducing and/or oxidizing reaction conditions at a temperature between 600° C. and 2000° C., particularly at temperatures between 900° C. and 1100° C., the nitrogen bound in the ammonium sulfate is mainly reacted to $N_2$ with the simultaneous recovery of gaseous sulfur compounds ($SO_2$, $SO_3$, COS, $H_2S$, etc.). In Example 1 of the BASF patent, a 10% by weight ammonium sulfate solution is introduced through a burner with a centrally located atomization lance into an adiabatic, vertically placed combustion chamber, in which reducing conditions are established by appropriately controlling combustion. Natural gas is used as the fuel with 80% theoretical air, producing a combustion gas containing CO, $H_2$, $H_2S$, and zero NO. The flue gas is said to be conducted to a gas workup in which the gaseous sulfur compounds (COS and $H_2S$) are separated. The reference further reports that the purified sulfur-containing gases can be carried through a working unit in a subsequent process, e.g., reaction to elemental sulfur in a Claus unit. The remaining gas is used for the production of steam by the under-firing of a boiler or can be used for heating purposes by subsequent combustion. Other examples describe oxidative combustion of the ammonium sulfate solution.

The ammonium sulfate solutions used in the process of DE 41 01 497 are relatively dilute, thereby requiring a substantial energy input for vaporization of water, and producing a combustion gas in which sulfur-bearing gases are diluted with water vapor and other products of combustion. Although Example 1 of the '497 publication states that the hydrogen sulfide produced in the reductive combustion can be converted to sulfur in a Claus unit, the hydrogen sulfide content of the combustion gas is relatively low. The '497 publication does not describe measures to maximize either the hydrogen sulfide, carbon monoxide, or hydrogen content of the combustion gas.

In U.S. Pat. No. 4,208,390, Hirabayashi et al. describe a process for the recovery of ammonia and sulfur dioxide from an aqueous mixture containing an ammonium salt of sulfuric acid obtained as a by-product of the preparation of ε-caprolactam or cyclohexanone oxime. The by-product mixture comprises a roughly 50% by weight aqueous solution of ammonium bisulfate, and is reacted, in finely divided form, at a temperature of 700° to 950° C. with gases obtained from the combustion of a fuel and a controlled amount of oxygen, releasing ammonia and sulfur dioxide which are thereafter separated from the reaction mixture. The amount of oxygen is controlled to about 96% of the theoretical oxygen, i.e., the amount of oxygen that would be required to convert the nitrogen, sulfur, hydrogen and carbon contained in the by-product mixture and fuel into, respectively, $N_2$, $SO_2$, $H_2O$, and $CO_2$. The reaction gas discharged from the combustion furnace was reported to contain ammonia and 95.6% of the $SO_2$ that theoretically could have been formed, 4.6% of the sulfur contained in the feed mixture having been converted to $SO_3$.

Diaz-Bossio et al., "Reductive Decomposition of Calcium Sulfate Utilizing Carbon Monoxide and Hydrogen, *Chem. Eng. Sci.*, Vol. 40, No. 3, pp. 319–324, describe thermal reduction of calcium sulfate to calcium sulfide using carbon monoxide and hydrogen produced by reforming methane. Other references disclose that sodium sulfate can be reduced to sodium sulfide by use of hydrogen, Birk et al. "Hydrogen Reduction of Alkali Sulfate," *Ind. Eng. Chem. Proc. Des. Dev.*, 10(1), pp. 7–13 (1971), Nyman and O'Brien, "Catalytic Reduction of Sodium Sulfate," *Ind. Eng. Chem.*, 39(8), pp. 1021–1023 (1947), and White and White, "Manufacture of Sodium Sulfide," *Ind. Eng. Chem.*, 28(1), pp. 244–246; or with carbon monoxide, Li and Heinigen, "Kinetics of Sodium Sulfate Reduction in the Solid State by Carbon Monoxide," *Chem. Eng. Sci.*, 43(8), pp. 2079–2085 (1988) and Zou et al., "Carbon Monoxide Reduction of Sodium Sulfate Mixed with Sodium Titanate," *Can. J. Chem. Eng.*, pp. 892–893 (1993).

SUMMARY OF THE INVENTION

Among the several objects of the present invention may be noted the provision of a process for the destruction of aqueous by-products containing ammonium salts of sulfuric acid, in particular such by-products as are produced in the manufacture of methionine and HMBA; the provision of such a process in which reductive combustion is carried out at relatively high energy efficiency; the provision of such a process which converts sulfur contained in the aqueous by-products to a divalent sulfur compound; the provision of such a process which yields divalent sulfur compounds that can be converted to other useful sulfur-bearing products; the provision of such a process which produces a combustion gas containing significant concentrations of hydrogen sulfide and/or other divalent sulfur compounds; the provision of such a process which yields sulfur-bearing products that can be used as raw materials in the preparation of methionine or HMBA, and in particular raw materials that can be recycled for use in the methionine or HMBA manufacturing process.

Briefly, therefore, the present invention is directed to a process for destruction of an aqueous mixture containing an ammonium salt of sulfuric acid. An aqueous feed mixture containing ammonium ion in a proportion of at least 3% by weight and a sulfur-bearing component selected from among sulfate ion, bisulfate ion and sulfuric acid in a total proportion of at least about 10% by weight, expressed as $SO_4^{-2}$, is introduced into a reductive combustion zone, thereby producing a combustion gas containing a divalent sulfur compound in a concentration of at least about 4500 ppm by volume, dry gas basis.

The invention is further directed to a process for recovery of a divalent sulfur compound from an aqueous mixture containing an ammonium salt of sulfuric acid. An aqueous feed mixture comprising an ammonium salt of sulfuric acid is introduced along with an oxygen-containing gas into a reductive combustion zone thereby producing a combustion gas containing hydrogen sulfide; and hydrogen sulfide produced in the combustion gas is converted to a divalent sulfur compound.

The invention is further directed to a process for preparation of an a-substituted carboxylic acid compound selected from methionine and 2-hydroxy-4-methylthiobutanoic acid. Methyl mercaptan is reacted with acrolein to produce 3-methylthiopropanal, and 3-methylthiopropanal is reacted with hydrogen cyanide to produce 2-hydroxy-4-methylthiobutanenitrile. Optionally, 2-hydroxy-4-methylthiobutanenitrile is reacted with ammonia to produce 2-amino-4-methylthiobutanenitrile. A hydrolysis substrate selected from among 2-hydroxy-4-methylthiobutanenitrile and 2-amino-4-methylthiobutanenitrile is contacted with a hydrolyzing acid selected from among sulfuric acid, ammonium bisulfate and mixtures thereof to produce an α-substituted carboxylic acid product selected from 2-hydroxy-4-methylthiobutanoic acid and methionine and a by-product ammonium salt of sulfuric acid. Carboxylic acid product and ammonium salt are separated from the hydrolyzate. An aqueous feed mixture containing the separated ammonium salt is introduced into a reductive combustion zone thereby producing a combustion gas containing hydrogen sulfide. Hydrogen sulfide produced in the combustion gas is converted to methyl mercaptan; and methyl mercaptan is recycled for reaction with acrolein.

The invention is further directed to a process for the preparation of an a-substituted carboxylic acid compound selected from methionine and 2-hydroxy-4-methylthiobutanoic acid. Methyl mercaptan is reacted with acrolein to produce 3-methylthiopropanal. 3-Methylthiopropanal is reacted with hydrogen cyanide to produce 2-hydroxy-4-methylthiobutanenitrile. Optionally, 2-hydroxy-4-methylthiobutanenitrile is reacted with ammonia to produce 2-amino-4-methylthiobutanenitrile. A hydrolysis substrate selected from 2-hydroxy-4-methylthiobutanenitrile and 2-amino-4-methylthiobutanenitrile is contacted with a hydrolyzing acid selected from sulfuric acid, ammonium bisulfate and mixtures thereof to produce an α-substituted carboxylic acid product selected from 2-hydroxy-4-methylthiobutanoic acid and methionine and a by-product ammonium salt of sulfuric acid. Carboxylic acid product and ammonium salt are separated from the hydrolyzate and an aqueous feed mixture containing the ammonium salt is introduced into a reductive combustion zone thereby producing a combustion gas containing hydrogen sulfide. The combustion gas containing hydrogen sulfide is contacted with a further supply of oxygen containing gas in a secondary combustion zone thereby producing a secondary combustion gas comprising sulfur dioxide. Sulfur dioxide produced in the secondary combustion zone is contacted with oxygen over an oxidation catalyst to produce a conversion gas containing sulfur trioxide; and sulfur trioxide is contacted with sulfuric acid in an $SO_3$ absorption zone to produce an absorption acid containing incremental sulfuric acid produced in a liquid phase on absorption.

The invention is further directed to a process for the preparation of an α-substituted carboxylic acid compound selected from methionine and 2-hydroxy-4-methylthiobutanoic acid. Methyl mercaptan is reacted with acrolein to produce 3-methylthiopropanal. 3-Methylthiopropanal is reacted with hydrogen cyanide to produce 2-hydroxy-4-methylthiobutanenitrile. Optionally, 2-hydroxy-4-methylthiobutanenitrile is reacted with ammonia to produce 2-amino-4-methylthiobutanenitrile. A hydrolysis substrate selected from 2-hydroxy-4-methylthiobutanenitrile and 2-amino-4-methylthiobutanenitrile is contacted with a hydrolyzing acid selected from sulfuric acid, ammonium bisulfate and mixtures thereof to produce an α-substituted carboxylic acid product selected from 2-hydroxy-4-methylthiobutanoic acid and methionine and a by-product ammonium salt of sulfuric acid. Carboxylic acid product and ammonium salt are separated from the hydrolyzate and an aqueous feed mixture containing the ammonium salt is introduced into a reductive combustion zone thereby producing a combustion gas containing hydrogen sulfide. The combustion gas containing hydrogen sulfide is contacted with a further supply of oxygen containing gas in a secondary combustion zone thereby producing a secondary combustion gas comprising sulfur dioxide. Sulfur dioxide produced in the secondary combustion zone is contacted with hydrogen peroxide to produce sulfuric acid.

The invention is still further directed to a process for the preparation of an α-substituted carboxylic acid compound selected from methionine and 2-hydroxy-4-methylthiobutanoic acid. Methyl mercaptan is reacted with acrolein to produce 3-methylthiopropanal. 3-methylthiopropanal is reacted with hydrogen cyanide to produce 2-hydroxy-4-methylthiobutanenitrile. Optionally, 2-hydroxy-4-methylthiobutanenitrile is reacted with ammonia to produce 2-amino-4-methylthiobutanenitrile. A hydrolysis substrate selected from 2-hydroxy-4-methylthiobutanenitrile and 2-amino-4-methylthiobutanenitrile is contacted with a hydrolyzing acid selected from sulfuric acid, ammonium bisulfate and mixtures thereof to produce an α-substituted carboxylic acid product selected from 2-hydroxy-4-methylthiobutanoic acid and methionine and a by-product ammonium salt of sulfuric acid. Carboxylic acid product and ammonium salt are separated from the hydrolyzate and an aqueous feed mixture containing the ammonium salt is introduced into an incinerator. The ammonium salt is oxidized in the incinerator to produce an oxidative combustion gas comprising sulfur dioxide. The sulfur dioxide produced in the incinerator is contacted with a hydrocarbon gas comprising methane, thereby producing a process gas comprising carbon oxides, hydrogen sulfide and hydrogen. The carbon oxides, hydrogen sulfide and hydrogen contained in the process gas are passed through a catalytic reaction zone to form methyl mercaptan, which is recycled for reaction with acrolein.

Other objects and features will be in part apparent and in part pointed out hereinafter.

BRIEF DESCRIPTION OF THE DRAWINGS

FIG. 9A is a collection of chromatograms showing the sulfur species detected in the combustion gas produced by the 50% stoichiometry combustion runs of Example 6;

Corresponding reference characters indicate corresponding parts throughout the several views of the drawings.

DESCRIPTION OF THE PREFERRED EMBODIMENTS

Figure 1:
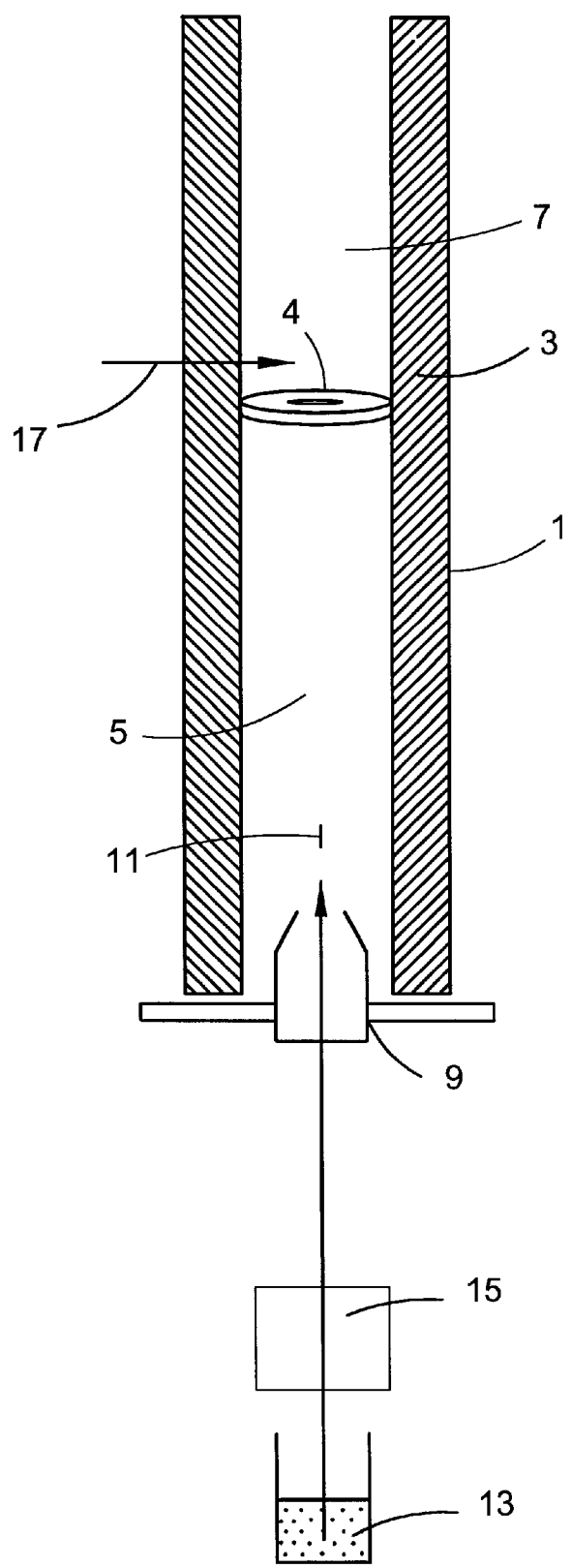
FIG. 1 is a schematic diagram illustrating an apparatus for the combustion of sulfuric acid and/or ammonium salts thereof.

In accordance with the present invention, processes have been discovered for the recovery of a divalent sulfur compound, particularly hydrogen sulfide and/or carbonyl sulfide from the reductive combustion of ammonium salts of sulfuric acid; and for the conversion of the divalent sulfur compounds produced in the combustion to other useful forms, including, for example, methyl mercaptan, sulfuric acid and elemental sulfur.

The process of the invention is implemented by introducing an aqueous feed mixture comprising ammonium bisulfate, ammonium sulfate or mixtures thereof into a reductive combustion zone. The feed mixture preferably contains at least about 3% by weight ammonium ion and at least about 10% by weight of the sum of sulfate ion, bisulfate ion, sulfuric acid and mixtures thereof, more preferably at least about 5% by weight ammonium ion and at least about 15% by weight of the sum of sulfate ion, bisulfate ion, sulfuric acid, and mixtures thereof. For example, the feed mixture may comprise an aqueous solution containing at least about 30% by weight, preferably at least about 50% by weight ammonium bisulfate, which is typical of solutions that may be produced in the preparation of HMBA per U.S. Pat. No. 4,524,077. Alternatively, the feed mixture may contain at least about 20% by weight ammonium sulfate, as produced, for example, in the synthesis of methionine, or in the production of HMBA per the process of U.S. Pat. No. 4,912,257. A relatively high concentration of ammonium salt is advantageous in minimizing the energy requirement for vaporization of water contained in the feed mixture, and allows the formation of a reductive combustion gas having a relatively high concentration of reduced sulfur compounds, e.g., compounds of divalent sulfur. Consistent with good combustion practice, the content of ash-forming materials in the feed solution should be minimized.

A fuel, preferably a hydrocarbon fuel such as natural gas, propane or butane is also introduced into the combustion zone together with an oxygen-containing gas, preferably air, or in some cases oxygen-enriched air. The fuel, aqueous feed mixture and oxygen-containing gas are introduced into the combustion zone in such relative proportions that the oxygen is less than that theoretically required for complete oxidation of the fuel and other oxidizable components entering the zone. Preferably, oxygen enters the combustion zone at a rate which is not greater than about 80%, preferably not greater than about 75%, of the theoretical oxygen rate necessary to oxidize the fuel, ammonium salt and other oxidizable components to $CO_2$, $H_2O$, $SO_2$ and $N_2$. It has been found that above a threshold rate that generally falls from about 70% to about 80% of theoretical, any increase in the relative rate of oxygen-containing gas causes a precipitous drop in the concentration of divalent sulfur compound, particularly hydrogen sulfide, in the combustion gas. Using the relatively concentrated ammonium salt solutions described herein, it has been found feasible to sustain the reductive combustion at oxygen supply rates approaching values as low as about 40% of theoretical. More preferably, the combustion is operated using from about 60% to about 75% theoretical oxygen.

Fuel is introduced into the combustion zone to support the combustion and maintain the combustion temperature within a preferred range of about 900° to about 1400° C. More preferably, the temperature is maintained within about 1100° to about 1400° C. Aqueous feed mixture may be introduced at a rate of at least about 1.0 kg/m³ fuel (STP), preferably at least about 1.2 kg/m³ (STP), more preferably at a rate of at least about 1.4 kg/m³ (STP). At the relatively high concentrations of ammonium salts maintained in the feed mixture, it has been discovered that the reductive combustion can be conducted at a relatively high ratio of at least about 2 gram-moles salt per cubic meter fuel (at standard temperature and pressure), preferably at least about 5 gram-moles salt per cubic meter fuel (STP), more typically from about 7 to about 11 gram-moles salt per standard cubic meter fuel, thereby producing hydrogen sulfide and/or other divalent sulfur compound (essentially entirely COS) at a rate of at least about 2, preferably at least about 5, gram-moles/m³ fuel (STP), typically from about 7 to about 11 gram-moles/m³ fuel (STP). Moreover, on a dry gas basis, the combustion gas produced in the process of the invention contains at least about 4500 ppm by volume, preferably from about 0.5 vol % to about 5 vol %, divalent sulfur compound, which in most instances comprises predominantly hydrogen sulfide, the remainder being substantially carbonyl sulfide. The content of divalent sulfur compound in the combustion gas is controlled by the relative proportions of fuel, aqueous feed mixture and oxygen-containing gas introduced into the combustion zone. By operation with a significant deficiency of air as noted above, a combustion gas is obtained which may also contain from about 1 vol % to about 4.5 vol % hydrogen sulfide; at least about 0.1 vol %, preferably from about 0.1 vol % to about 1 vol % carbonyl sulfide; at least about 2 vol %, preferably from about 4 vol % to about 10 vol % carbon monoxide; at least about 1 vol %, preferably from about 3 vol % to about 5 vol % hydrogen; and, at least about 10 vol %, preferably from about 10 vol % to about 15 vol % carbon dioxide, all on a dry gas basis. Even higher concentrations of $H_2S$, COS, $H_2$, CO and $CO_2$ can be realized by carrying out the combustion with oxygen-enriched air, e.g., an oxygen-containing gas mixture comprising from about 25 vol % to about 50 vol % oxygen.

It has been found that when the reductive combustion as described above is conducted in a combustion chamber lined with a refractory containing compositions comprising aluminum or titanium, the divalent sulfur compound in the combustion gas primarily comprises hydrogen sulfide with minimal carbonyl sulfide present. Without being limited to a particular theory, it is believed that a composition comprising oxides of aluminum or titanium (e.g., aluminum oxide or titanium dioxide) acts as a catalyst in preferentially reducing sulfur dioxide in the combustion gas to hydrogen sulfide. As the combustion gas contacts the catalyst within a catalytic conversion zone, it is believed that the catalyst promotes the preferential conversion of sulfur dioxide in the combustion gas to hydrogen sulfide according to the following equation:

$$SO_2 + 3H_2 \rightarrow H_2S + H_2O$$

Other participating reactions include:

$$CH_4 + H_2O \rightarrow CO + 2H_2$$

$$H_2S + CO \rightarrow H_2 + COS$$

$$CH_4 \rightarrow C + H_2$$

$$2C + SO_2 \rightarrow COS + CO$$

When the combustion gas is contacted with a catalyst in a catalytic conversion zone, the catalyst provides for a higher ratio of hydrogen sulfide to carbonyl sulfide in the combustion gas than the hydrogen sulfide to carbonyl sulfide ratio that would prevail if the combustion gas did not contact such a catalyst under otherwise identical combustion conditions. Use of a catalyst allows the molar ratio of hydrogen sulfide to carbonyl sulfide in the combustion gas to be at least about 1:1, preferably at least about 4:1, and more preferably at least about 10:1. Likewise, contacting the combustion gas with a catalyst allows the molar ratio of hydrogen sulfide to sulfur dioxide in the combustion gas to be at least about 1.5:1, preferably at least about 10:1, more preferably at least about 40:1 and even more preferably at least about 80:1.

Catalysts effective to promote the formation of hydrogen sulfide in the combustion gas may include compositions comprising oxides of aluminum or titanium (e.g., aluminum oxide or titanium dioxide). Alternatively, the catalytic conversion zone may contain a composition comprising metal sulfides such as transition metal sulfides (e.g., FeS, $MoS_2$, or $WS_2$) to catalyze the formation of hydrogen sulfide in the combustion gas. As noted above, the catalyst may be present in the lining of the combustion chamber as a component of a refractory material comprising mixed metal oxides including oxides of aluminum or titanium. For example, a suitable refractory material is Kaolite 2300-LI, a castable refractory commercially available from Thermal Ceramics of Augusta, Ga. In such an embodiment, the combustion zone and the catalytic conversion zone are substantially coextensive.

Although a catalytic conversion zone consisting of a catalytic refractory lining the combustion chamber as described above may be used to obtain a higher concentration of hydrogen sulfide in the combustion gas, it has been found that soot may form in the combustion so that, over time, the active catalyst sites in the refractory may become covered with carbon. This results in an increasing concentration of carbonyl sulfide in the combustion gas leaving the chamber. Thus, to ensure that the divalent sulfur compound obtained in the combustion of the present invention is primarily hydrogen sulfide, accumulated carbon must be periodically removed from the combustion chamber.

In an alternative embodiment, catalyst in addition to or as a substitute for catalyst present in the refractory lining the combustion chamber may be used to promote the reduction of sulfur dioxide in the combustion gas. The additional catalyst may be a composition comprising an oxide of aluminum or titanium, preferably activated alumina as described in Sarlis and Berk, "Reduction of Sulfur Dioxide with Methane over Activated Alumina", Ind. Eng. Chem. Res., 1988, vol. 27, pp. 1951–1954, or a metal sulfide, preferably FeS, $MoS_2$ or $WS_2$, as described by Mulligan and Berk, "Reduction of Sulfur Dioxide with Methane over Selected Transition Metal Sulfides", Ind. Eng. Chem. Res., 1989, vol. 28, pp. 926–931. The presence of additional catalyst extends the effective catalyst life in the combustion chamber and decreases the frequency with which it is necessary to remove carbon from the combustion chamber and other catalyst surfaces to maintain satisfactory conversion to hydrogen sulfide. It is contemplated that one skilled in the art could easily extend the life of the combustion chamber by controlling the amount of catalyst employed for a particular feed solution while optimizing the desired ratio of hydrogen sulfide to carbonyl sulfide produced in the combustion gas.

Any apparatus generally known in the art for contacting a gas over a catalyst is suitable for use in the present invention. The catalyst may be present inside the combustion chamber such that the combustion zone comprises the catalytic conversion zone. For example, catalytic baffles may extend into the flow of combustion gas within the combustion zone. Alternatively, the combustion gas may contact a packed bed or a fluidized bed of catalytic particles within the combustion zone to provide for more catalyst surface area than catalytic baffles. Preferably, a practical commercial embodiment is designed to achieve sustained operation and avoid excessive process downtime resulting from shutdown required for removal of carbon. For example, an embodiment effective for sustained commercial operation may comprise parallel packed columns wherein one column is in contact with the combustion gas while the spent catalyst of the parallel column is regenerated. Another example may include a progressively rising fluidized bed wherein catalyst exiting the top of the reactor is separated from the combustion gas and circulated through a regeneration unit in which carbon is burned off the catalyst.

The temperature at which the combustion gas is contacted with the catalyst within the catalytic conversion zone depends upon the location of the catalytic conversion zone with respect to the reductive combustion zone. For example, the temperature of the combustion gas cools as it flows away from the combustion flame. Typically, a combustion chamber used in the present invention has a temperature profile ranging from about 900° to about 1400° C. near the combustion flame to about 400° to about 850° C. near the combustion gas exit.

In accordance with a particularly preferred embodiment, the combustion gas is contacted with catalyst outside of the combustion zone in addition to the catalyst present in the refractory lining the combustion chamber to maximize the catalyst surface area for contact with the combustion gas. In such an embodiment, the catalytic conversion zone extends outside of the combustion chamber such that the exit of the catalytic conversion zone is downstream of the combustion zone with respect to the flow of combustion gas. Alternatively, if the combustion zone is free of catalyst, the inlet of the catalytic conversion zone is downstream of the combustion zone with respect to the flow of combustion gas.

As discussed above, any apparatus generally known in the art for contacting a gas with a catalyst may be suitable for contacting the combustion gas with catalyst outside of the combustion zone. The combustion gas exiting the combustion chamber is directly contacted with the catalyst at a temperature of about 400° to about 850° C., preferably about 550° to about 750° C., to reduce the sulfur dioxide content and to increase the concentration of hydrogen sulfide such that hydrogen sulfide constitutes at least about 50 percent of the total sulfur species in the combustion gas, more preferably at least about 80 percent of the total sulfur species in the combustion gas.

Operation under the reductive combustion conditions outlined above is effective to oxidize substantially all ammonia contained in the feed mixture to nitrogen ($N_2$) and either hydrogen ($H_2$) or water vapor. Ammonia content of the combustion gas is less than about 0.25 ppm by volume. Moreover, carrying out the combustion under reductive conditions has been demonstrated to be effective in substantially entirely eliminating the formation of $NO_x$ in the combustion. The combustion gas exiting the reductive combustion zone may be introduced along with a further stream of oxygen-containing gas into a secondary combustion zone under oxidative conditions to fully oxidize divalent sulfur compounds to $SO_2$ and/or $SO_3$, carbon monoxide to carbon dioxide, and hydrogen to water vapor. It has been found that the $NO_x$ content of the combustion gas exiting the oxidative combustion zone remains low, i.e., less than about 125 ppm by volume, which is essentially reflective of thermal oxidation of nitrogen substantially without significant conversion of ammonia nitrogen to $NO_x$.

Illustrated in FIG. 1 is an apparatus effective for the two stage combustion process of the present invention. An adiabatic incinerator 1 comprises a vertical cylindrical tube 3 constituted of refractory material. A ceramic frit or blanket 4 divides tube 3 into a lower primary combustion zone 5 and an upper secondary combustion zone 7. A burner 9 is aligned axially and concentrically of tube 3 in the lower end thereof and oriented for upward discharge of air and fuel, and upward flow of combustion gas, through the primary combustion zone. Primary air and fuel (e.g., propane) are separately supplied to burner 9 from sources not shown. A lance 11 is positioned concentrically of both tube 3 and burner 9 for injection of aqueous feed solution axially of the tube and upwardly into primary combustion zone 7 5 generally in the region of the flame emanating from burner 9. An ammonium bisulfate solution, ammonium sulfate solution, mixed salt solution, ammonium sulfate suspension, and/or sulfuric acid is delivered to the combustion zone 7 from a reservoir 13 through lance 11 by operation of an aqueous feed mixture pump 15. Air is introduced into burner 9 at a rate preferably less than the theoretical requirement to fully oxidize the fuel and all components of the aqueous feed mixture entering the primary combustion zone 7. More preferably, less than about 80% of the theoretical requirement for air is introduced, so that the primary combustion zone 7 operates reductively, producing a combustion gas that preferably contains at least about 4500 ppm by volume hydrogen sulfide, from about 1 vol % to about 5 vol % hydrogen, and from about 2 vol % to about 10 vol % carbon monoxide. Substantially all ammonia is oxidized to $N_2$, hydrogen and water vapor. Formation of $NO_x$ is essentially nil, i.e., less than about 50 ppm by volume.

Secondary air may be introduced through an air inlet 17 into upper combustion zone 7 so that oxidative combustion can be conducted in the latter zone to convert substantially all divalent sulfur compound to $SO_2$ or $SO_3$, substantially all hydrogen to water vapor, and substantially all carbon monoxide to $CO_2$, while continuing to minimize formation of $NO_x$. The two stage combustion process of the present invention is highly suitable for use in the spent acid recovery processes as described in U.S. Pat. Nos. 5,498,970 and 5,670,128 which are expressly incorporated herein by reference. In accordance with the process of the '970 and '128 patents, the secondary combustion gas of the present invention is optionally cleaned and cooled for condensation of water vapor, then passed through a catalytic converter for conversion of $SO_2$ to $SO_3$, following which the $SO_3$ is absorbed in a concentrated sulfuric acid stream wherein it reacts with water to form additional sulfuric acid.

Alternatively, the combustion gas produced in the primary, i.e., reductive, combustion zone may be removed from the incinerator and processed for recovery of hydrogen sulfide or other divalent sulfur compound produced in the combustion, or further processed for conversion of the divalent sulfur compound to another useful sulfur product. For example, $H_2S$ may be recovered from the combustion gas by absorption in a suitable solvent, followed by desorption to yield a desorption gas stream containing $H_2S$ in high concentration. Such absorption processes are described, for example, in U.S. Pat. Nos. 3,590,555 and 5,304,361 which are expressly incorporated herein by reference.

Figure 2:
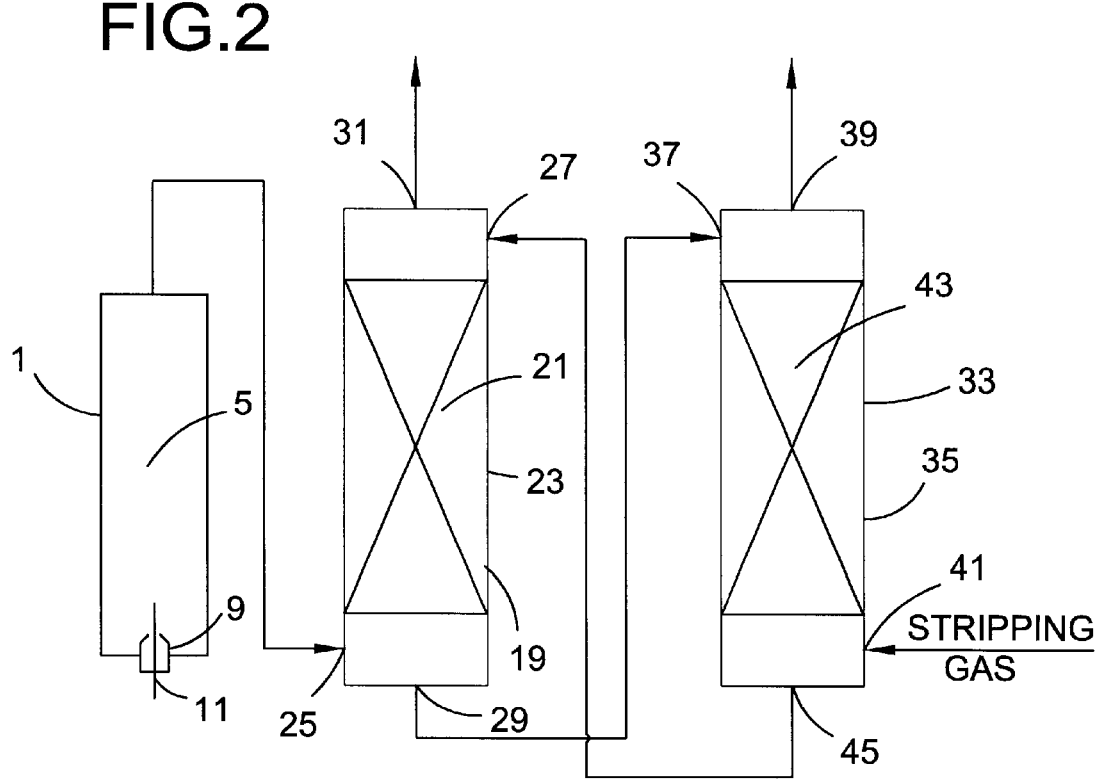
FIG. 2 is a schematic flowsheet of a process for producing a combustion gas containing hydrogen sulfide and recovering the hydrogen sulfide in concentrated form through an absorption/desorption cycle.

FIG. 2 illustrates a process for concentrating hydrogen sulfide via an absorption/desorption cycle. A combustion gas comprising hydrogen sulfide is produced in a reductive combustion zone 5. The combustion gas is cooled in a surface condenser (not shown), separated from any aqueous condensate formed in cooling, optionally cleaned in a conventional manner, and thereafter contacted with an amine or other liquid solvent for hydrogen sulfide in an absorber 19. Absorber 19 comprises a gas/liquid contact zone 21 comprising means, such as packing, for promoting mass transfer between the gas phase and the liquid phase, and is typically contained within a vertical tower 23. Tower 23 has a gas inlet 25 in gas flow communication with reductive combustion zone 5 and a liquid inlet 27 for the solvent. Hydrogen sulfide is transferred from the gas phase to the liquid phase in zone 21 of the absorber 19, producing a rich absorption liquor containing hydrogen sulfide. Rich absorption liquor is removed from the absorber 19 via liquid outlet 29 of tower 23. The gas phase, which has been substantially stripped of hydrogen sulfide is removed via exit 31 of tower 23 for further processing, e.g., by passage through a secondary combustion zone wherein reduced components of the gas stream such as carbon monoxide and hydrogen may be oxidized.

The rich absorption liquid is transferred to a stripper 33 wherein hydrogen sulfide is removed from the liquid phase by heating thereof and/or by contact with a stripping gas, thereby producing a desorption gas stream containing hydrogen sulfide. The temperature and rate of flow of any stripping gas are controlled so that the concentration of hydrogen sulfide in the desorption gas stream is at least about 5 times, more preferably at least about 15 times, the concentration of hydrogen sulfide in the combustion gas. Preferably the desorption gas $H_2S$ concentration is at least about 30 vol %, typically at least about 70% by vol., more preferably at least about 90% by volume, on a dry gas basis. Stripper 33 comprises a tower 35 having a liquid inlet 37 in liquid flow communication with the liquid outlet 29 of tower 23 and a gas outlet 39 for the desorption gas. A stripping medium, e.g., an inert stripping gas and/or live steam used to promote removal of hydrogen sulfide from the liquid phase may be introduced via a gas inlet 41 of tower 33, and the tower may further comprise a gas/liquid contact zone 43 containing means for promoting mass transfer of hydrogen sulfide between the liquid phase and a stripping gas. Desorption produces a lean absorption solvent which is removed from the absorber 19 via tower liquid exit 45 and recycled to inlet 27 of absorption tower 23 to serve as solvent for the absorption of hydrogen sulfide from the combustion gas.

Alternatively, the absorption/desorption system may operate on a pressure swing principle. Cooled and optionally cleaned combustion gas is compressed and introduced into an absorber where it is contacted with solvent. The resulting rich absorption liquor is let down into a desorber operated under vacuum, or in any case at a pressure significantly lower than the pressure of the absorber. Reduction of the pressure results in desorption of hydrogen sulfide, yielding a desorption gas comprising hydrogen sulfide in relatively high concentration.

According to further alternatives, hydrogen sulfide may be recovered from the reductive combustion gas by membrane separation processes, using a series of semi-permeable membranes in a fractionation system by which the hydrogen sulfide can ultimately be isolated both from gases which diffuse more rapidly than hydrogen sulfide through a solid microporous membrane and from gases which diffuse more slowly.

Hydrogen sulfide produced in the reductive combustion can be converted to other useful sulfur compounds. For example, either the combustion gas or the desorption gas stream produced in the process of FIG. 2 may be introduced into a process for the preparation of methyl mercaptan by reaction of hydrogen sulfide with methanol, as described in EPO patent 0 850 922 or EPO patent 0 850 923, expressly incorporated herein by reference. Alternatively, hydrogen sulfide and carbon oxides obtained in the reductive combustion gas may be reacted in the presence of an appropriate catalyst to produce methyl mercaptan, using a process of the type described in U.S. Pat. Nos. 4,410,731, 4,449,006, 4,570,020, 4,665,242 and/or 4,668,825, also expressly incorporated herein by reference.

Carbon monoxide and carbon dioxide may each be reacted with $H_2S$ and hydrogen over a catalyst for the reaction to produce methyl mercaptan:

$$CO+H_2S+2H_2 \rightarrow CH_3SH+H_2O$$

$$CO_2+H_2S+3H_2 \rightarrow CH_3SH+2H_2O$$

The reaction with carbon monoxide proceeds in the following manner:

$$CO + H_2S \rightarrow COS + H_2$$

$$COS + 3H_2 \rightarrow CH_3SH + H_2O$$

Although carbon monoxide is more reactive and produces methyl mercaptan in higher yield, carbon dioxide in the combustion gas may also serve as a carbon source and contribute to the overall reaction optionally, elemental sulfur can be introduced into the feed gas to a catalytic reactor for the preparation of methyl mercaptan, in which case the desired product may also be produced by the following reactions:

$$CO + S + 3H_2 \rightarrow CH_3SH + H_2O$$

$$CO_2 + S + 4H_2 \rightarrow CH_3SH + 2H_2O$$

Elemental sulfur may be readily vaporized into the reductive combustion gas stream by contacting the gas stream with molten sulfur. Since hydrogen sulfide, the sulfur source in the combustion gas, is generally the limiting reactant in the methyl mercaptan synthesis, addition of elemental sulfur may be desirable to increase the productivity of the reaction. In an HMBA process in which methyl mercaptan produced from the combustion gas is recycled for preparation of MMP, incorporation of a supplemental source of sulfur may be necessary to assure production of methyl mercaptan at a rate sufficient to supply the demand therefor. Depending on methyl mercaptan yields, and on the overall material balance of the integrated process, it may be desirable to introduce elemental sulfur as a supplemental sulfur source. If a significant excess of sulfuric acid is used in the hydrolysis of HMBN to HMBA, sulfuric acid alone may serve as the sulfur source for the process. However, regardless of methyl mercaptan yields, a net supply of sulfur is necessary in a process wherein the ratio of sulfuric acid to HMBN in the hydrolysis is less than 1.0.

Figure 3:
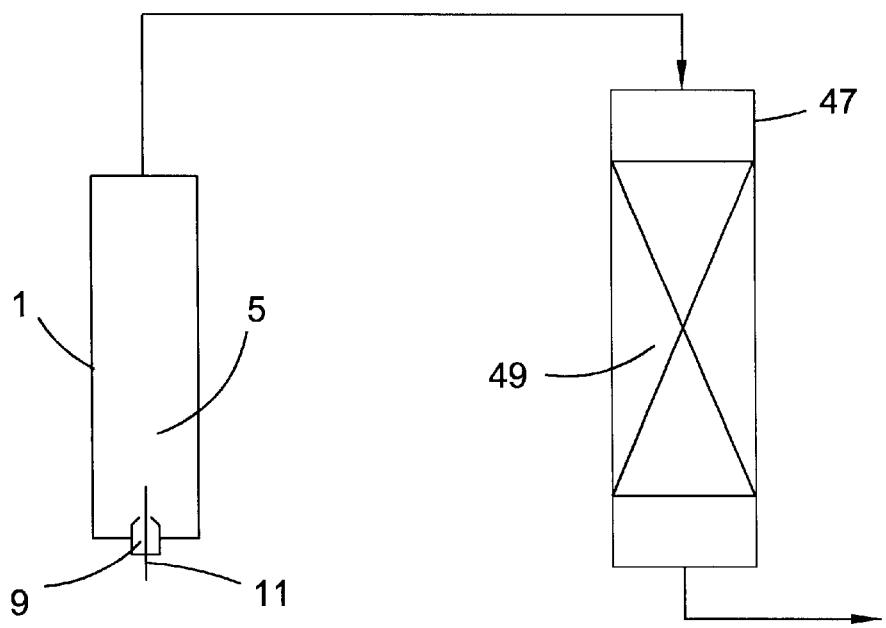
FIG. 3 is a schematic flowsheet illustrating an embodiment of the process of the invention for producing a combustion gas containing hydrogen sulfide and carbon dioxide, and converting them to methyl mercaptan.

FIG. 3 illustrates a process of the invention for the preparation of methyl mercaptan by reaction of hydrogen sulfide and carbon monoxide produced in the combustion. The combustion gas exiting the reductive combustion zone of incinerator 1 forms a reaction feed gas for the preparation of methyl mercaptan, which can be produced according to a process as described in U.S. Pat. Nos. 4,449,006 or 4,668,825, both of which are expressly incorporated herein by reference. The combustion gas is cooled to condense water vapor therefrom, then compressed to at least about 100 psig, preferably at least about 150 psig, more preferably to between about 400 and about 1000 psig, then introduced into a methyl mercaptan reactor 47. As introduced into the methyl mercaptan reactor 47, the cooled and compressed combustion gas is preferably at a temperature of at least about 150° C., more preferably at least about 200° C., but preferably no greater than about 325° C. If the heat of compression causes the temperature of the gas to be increased significantly above 325° C., it is preferably cooled before being introduced into the reactor 47. If the temperature of the compressed gas is below 200° C., it is preferably reheated, e.g., by transfer of heat from combustion gas exiting the reductive combustion zone for partial cooling thereof, or by transfer of heat from the reaction product gas exiting the methyl mercaptan reactor 47. The methyl mercaptan reactor contains a fixed or fluidized catalyst bed 49 comprising a catalyst for the reaction of hydrogen sulfide with carbon oxides, or reaction of hydrogen sulfide with carbon oxides, sulfur and hydrogen, to produce a reaction gas containing methyl mercaptan. The catalyst may comprise rutile titania, preferably sulfided by passage of a divalent sulfur compound such as hydrogen sulfide, carbon disulfide or various thiols thereover prior to introducing the $H_2S/CO/CO_2/COS/H_2$ feed stream. Alternatively, the catalyst may be sulfided in situ by passage of the $H_2S/CO/CO_2/COS/H_2$ feed gas thereover at elevated temperature at the outset of methyl mercaptan production operations. Mixed anatase/rutile catalysts may also be used, but such mixed catalysts preferably have a high rutile content. Other catalysts useful in the reaction include sulfides of Mn, Fe, Ni, Zn, Cr, Co or Mo; and mixtures of such sulfides with an alkali metal sulfide as described in U.S. Pat. No. 4,410,731, expressly incorporated herein by reference. Optionally, the catalyst can be prepared as an Fe, Ni, Zn, Cr, Co or Mo oxide, and then sulfided in situ substantially as described for rutile catalyst. Other suitable catalysts include V, Nb, or Ta on a titania support.

The reaction is carried out at a temperature ranging from about 225° to about 400° C., preferably from about 250° to about 300° C. The process is operative within the full range of hydrogen sulfide to carbon oxide ratios that may be computed from the ranges of proportions of these components of the reductive combustion gas fed to the methyl mercaptan reactor. Space velocities may range up to about 5000 h$^{-1}$.

Conversion of hydrogen sulfide and carbon oxides to methyl mercaptan is promoted by maintaining a substantial fraction of hydrogen in the reaction feed gas. Preferably, the $CO/H_2S/H_2$ ratio in the feed gas is from about 1/1/1 to about 25/1/10. Where elemental sulfur is incorporated into the feed gas, the $CO/S/H_2S/H_2$ ratio is preferably from about 1/0.01/1/1 to about 25/1/1/10. By operation of the reductive combustion under oxygen-deficient conditions as described above, the combustion step can be readily controlled to provide the requisite $CO/H_2S$ ratio. Moreover, a sufficient $H_2/H_2S$ ratio can ordinarily be achieved in the same manner. Optionally, a supplemental source of hydrogen and/or sulfur is supplied to reactor 47 to increase the hydrogen and sulfur concentration in the feed gas to achieve the above concentration ratios, thereby facilitating attainment of the desired hydrogen partial pressure without requiring excessive total pressure. Total pressure requirements for the reactor 47 may further be reduced by the use of oxygen enriched air as the oxygen-containing gas fed to reductive combustion zone 5. Where an increased fraction of hydrogen is desired in the feed gas, it may be provided from an extraneous source such as, for example, synthesis gas or the hydrogen output from a chloralkali operation. U.S. Pat. No. 4,449,006 specifically proposes combining hydrogen sulfide and synthesis gas for the preparation of methyl mercaptan.

Reaction gas exiting reactor 47 is cooled and directed to methyl mercaptan recovery operations. Methyl mercaptan can be separated by condensation and distilled as necessary for separation from impurities. U.S. Pat. No. 5,866,721, expressly incorporated herein by reference, describes a process for recovering methyl mercaptan produced by reaction of hydrogen sulfide and methanol. This process can be adapted for recovery of methyl mercaptan from the reaction gas exiting reactor 47 in the process of FIG. 3. Thus, the reaction gas at a reactor exit pressure in the range of about 100 to about 1000 psig is cooled to a temperature effective to condense the water contained in the reaction mixture, i.e., typically about 40° to about 75° C. A primary aqueous condensate is separated from the gas phase which is thereafter further cooled, typically to about 10° to about 50° C. for condensation of methyl mercaptan, unreacted hydrogen sulfide and dimethyl sulfide. The vent gas from the second condenser is optionally contacted with methanol for absorption of methyl mercaptan and dimethyl sulfide remaining in the gas phase. Hydrogen sulfide can be recovered in a second absorption step by contact with a secondary methanol stream. As desired, the recovered hydrogen sulfide can be stripped from the methanol and recycled to the methyl mercaptan reactor. Absorbed methyl mercaptan can be stripped from the methanol absorbent and then mixed with the secondary condensate to produce a mixture which is distilled to remove low boilers from the methyl mercaptan. Optionally, methyl mercaptan can be removed initially from the reaction gas by absorption in a suitable solvent, and ultimately isolated by stripping from the solvent.

Optionally, a more concentrated feed to a methyl mercaptan reactor can be provided by first separating hydrogen sulfide from the reductive combustion gas stream per the absorption/desorption cycle of FIG. 2, thereby producing a relatively concentrated hydrogen sulfide desorption stream containing $H_2S$ in a proportion of about 50% to about 90% by volume, or greater; then combining the desorption gas stream with CO and hydrogen. In one embodiment of such a process, hydrogen and CO are supplied entirely in the form of synthesis gas. Alternatively, the reductive combustion gas may be divided into two streams, one of which is directed to an $H_2S$ absorption/desorption system, and the other of which is bypassed around that system and combined with the concentrated hydrogen sulfide stream exiting the desorption stripper to provide a feed gas for the methyl mercaptan reactor. In this way, the feed gas may be effectively enriched in hydrogen sulfide. For example, if about 50% to about 75% of the reductive combustion gas is routed to an absorption/desorption system, the concentration of hydrogen sulfide in the methyl mercaptan feed gas can be increased by a factor of about two to about four relative to the concentration in the combustion gas, i.e, into the range of from about 1.5% to about 8% by vol., dry gas basis, while remaining within the preferred ranges set forth above for the $CO/H_2S/H_2$ ratio. Even higher hydrogen sulfide content may be achieved by directing from about 75% to about 90% of the reductive combustion gas to an absorption/desorption cycle of the type shown in FIG. 2, the remainder again being by-passed for mixing with the $H_2S$ desorption gas to form the methyl mercaptan reactor feed gas. However, at some point the by-pass stream becomes insufficient to supply other reactants, among which hydrogen is most likely to become limiting. If the by-pass fraction is further reduced to enhance hydrogen sulfide concentration, a supplemental source of hydrogen or other reactant may become necessary. Where synthesis gas is used as the source of hydrogen, it may be preferable to entirely dispense with the by-pass of reductive combustion gas, since synthesis gas also provides an ample supply of CO. However, if the source of supplemental hydrogen comprises a chloralkali or catalytic reforming operation, it is still useful to by-pass a fraction of the combustion gas to provide a source of CO. Tail gas from the $H_2S$ stripper of FIG. 2 may be directed to an oxidative combustion zone for destruction of hydrogen and CO contained therein.

Figure 4:
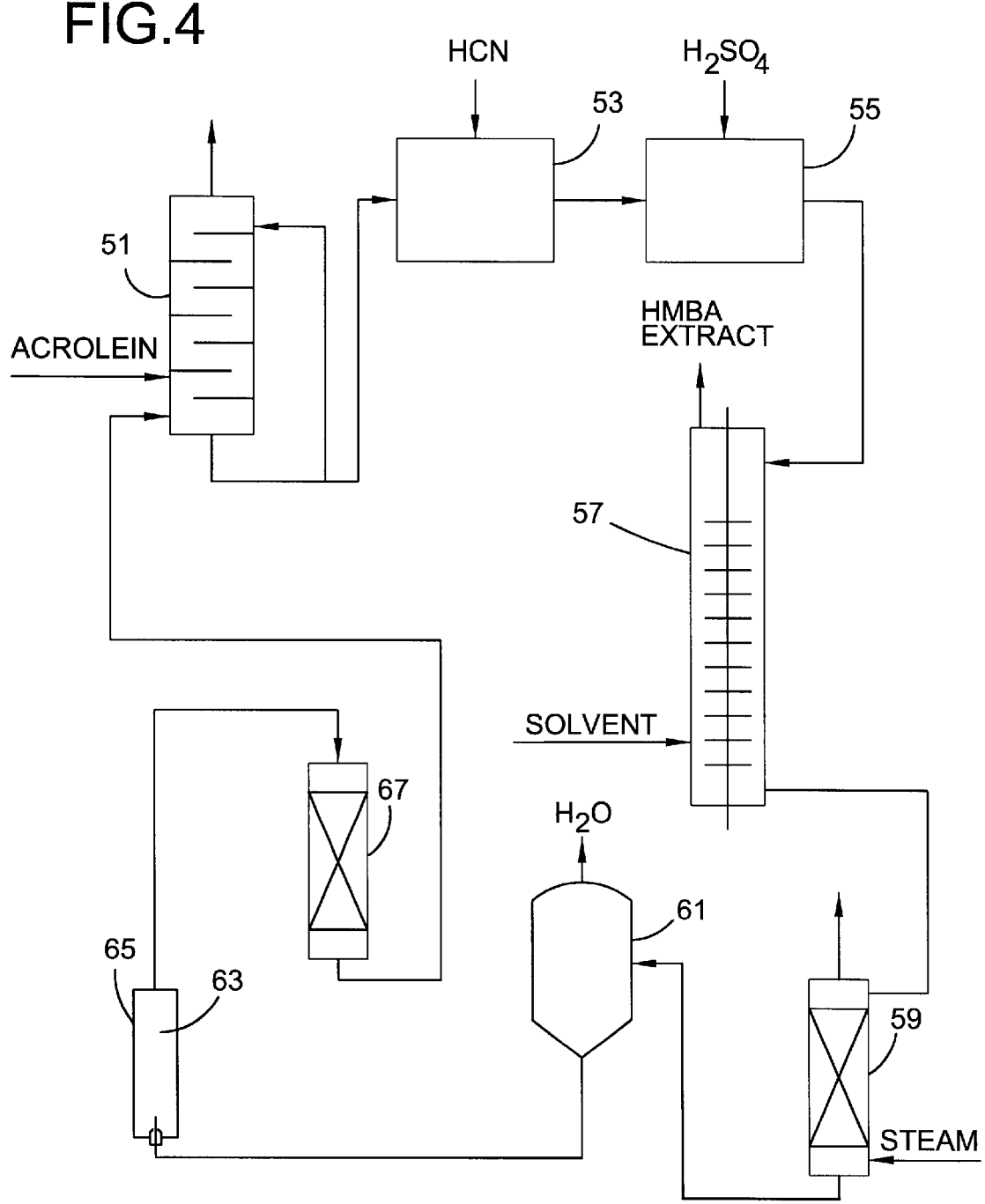
FIG. 4 is a schematic flowsheet illustrating the implementation of the process of FIG. 3 as part of a process for the manufacture of HMBA wherein methyl mercaptan is recycled.

FIG. 4 is a schematic flowsheet in which the process of FIG. 3 is integrated into a process for the manufacture of HMBA. Methyl mercaptan and acrolein are introduced into a reactor 51 where they are reacted to produce 3-methylthiopropanal (MMP). As described in U.S. Pat. Nos. 5,352,837, 5,637,766 and 5,905,171, all of which are expressly incorporated herein by reference, reactor 51 may comprise a co-current gas lift reactor in which both methyl mercaptan and acrolein are introduced into a liquid MMP reaction medium that is circulated rapidly between a vertical lift leg and a downcomer; or gaseous acrolein and MMP may be introduced into the lower or intermediate trays of a tray column through which the gas phase flows upwardly countercurrently to a downward flow of liquid MMP medium. Alternatively, the MMP may be prepared in a batch or semi-batch reaction from acrolein and methyl mercaptan. As further described in U.S. Pat. Nos. 5,637,766, 5,744,647 and 5,905,171, the MMP reactor 51 may comprise two stages, the second of which constitutes a finishing reactor for extinction of unreacted acrolein and/or methyl mercaptan exiting the first stage. Acrolein and methyl mercaptan react within the MMP medium in the presence of a catalyst to produce MMP, and net MMP product is withdrawn from reactor (reaction system) 51. Suitable catalysts for the reaction are disclosed, e.g., in U.S. Pat. Nos. 5,663,409 and 5,705,675.

MMP exiting reaction system 51 is contacted with hydrogen cyanide in a reactor 53, producing HMBN. A suitable process for the preparation of the nitrile is also disclosed in U.S. Pat. Nos. 5,663,409 and 5,705,675. HMBN from reactor 53 is converted to HMBA by a hydrolysis reaction system 55 using sulfuric acid to effect the hydrolysis. Other acidic sulfate solutions, including ammonium bisulfate or mixtures of ammonium bisulfate with ammonium sulfate or sulfuric acid may also be used in the hydrolysis. Conditions for hydrolysis with sulfuric acid are particularly disclosed in U.S. Pat. Nos. 4,524,077 and 5,856,567, both of which are expressly incorporated herein by reference. The hydrolyzate contains HMBA, ammonium bisulfate, either ammonium sulfate or sulfuric acid. The hydrolyzate is contacted with a substantially water-immiscible solvent in an extraction column 57 wherein HMBA is transferred from the aqueous phase to the solvent phase, yielding an extract containing the HMBA product and a raffinate containing the ammonium salt(s) and any free sulfuric acid. The raffinate typically contains from about 60% to about 70% by weight ammonium bisulfate, i.e., from about 9% to about 11% by weight ammonium ion and from about 50% to about 57% by weight bisulfate ion. The net flow of aqueous raffinate is steam distilled in a raffinate stripping column 59 for removal of residual solvent. The aqueous bottoms stream exiting column 59 typically contains from about 45% to about 50% by weight ammonium bisulfate, i.e., from about 7% to about 8% by weight ammonium ion and from about 38% to about 43% by weight bisulfate ion. Optionally, the raffinate stripper bottom stream is concentrated in a raffinate stripper bottom evaporator 61 to produce a solution containing from about 60% to about 80% by weight ammonium bisulfate (or from about 9% to about 12.5% by weight ammonium ion and from about 50% to about 68% by weight bisulfate ion). As desired, raffinate stripper bottoms may be concentrated by removing water in another conventional manner, e.g., reverse osmosis.

Hydrolysis of HMBN may also be carried out in the manner described in Hernandez, U.S. Pat. No. 4,912,257, expressly incorporated herein by reference. In the Hernandez process, HMBN is hydrolyzed with sulfuric acid to produce a hydrolyzate that is thereafter contacted with ammonia to neutralize some or all of the bisulfate ion, and thereby cause separation of the mixture into two liquid phases, one organic, the other aqueous. The organic phase comprises the HMBA product. The aqueous phase comprises a solution of ammonium sulfate which is concentrated to about 25% by weight, i.e., containing about 7% by weight ammonium ion to about 18% by weight sulfate ion, and removed from the process.

Either the ammonium bisulfate solution produced in the processes of U.S. Pat. Nos. 4,524,077 and 5,856,567 or the ammonium sulfate solution produced in the process of U.S. Pat. No. 4,912,257 may be introduced into a reductive combustion zone 63 of an incinerator 65, together with combustion air and fuel to support the combustion. Incinerator 65 may have a configuration similar to that of incinerator 1, except that incinerator 65 does not contain a secondary, oxidative combustion zone. Air is supplied at a rate not greater than about 80%, preferably from about 60% to about 75% of the rate necessary to provide oxygen in a proportion theoretically equivalent to the fuel, the ammonium salt, and other oxidizable components of the aqueous feed solution entering the combustion zone. The fuel preferably comprises propane or natural gas. Reductive combustion in zone 63 produces a combustion gas containing from about 0.5% to about 4.5% by volume hydrogen sulfide, from about 0.1% to about 1% by volume carbonyl sulfide, from about 4% to about 10% by volume carbon monoxide, from about 3% to about 5% by volume hydrogen, and from about 10% to about 15% by volume carbon dioxide, all measured on a dry gas basis. optionally, the air entering the combustion zone is enriched with oxygen so that it contains, e.g., from about 30% to about 50% oxygen, in which instance the combustion gas may contain from about 0.3% to about 6.5% by volume hydrogen sulfide, from about 10% to about 15% by volume carbon monoxide, up to about 1% by volume carbonyl sulfide, about 1% to about 0.5% by volume hydrogen, from about 10% to about 16% by volume carbon dioxide, dry basis. The combustion gas is introduced into methyl mercaptan reactor 67 wherein $H_2S$ and CO contained in the combustion gas are converted to methyl mercaptan. Optionally, the methyl mercaptan reactor feed stream may be further enriched as described above by passing a portion of the reductive combustion gas through an absorption/desorption cycle to separate $H_2S$, and combining the $H_2S$ desorption gas stream with the remainder of the combustion gas which is by-passed around the absorber. The methyl mercaptan obtained in the reaction gas stream exiting reactor 67 is recycled to MMP reactor 51 for further synthesis of MMP.

Figure 5:
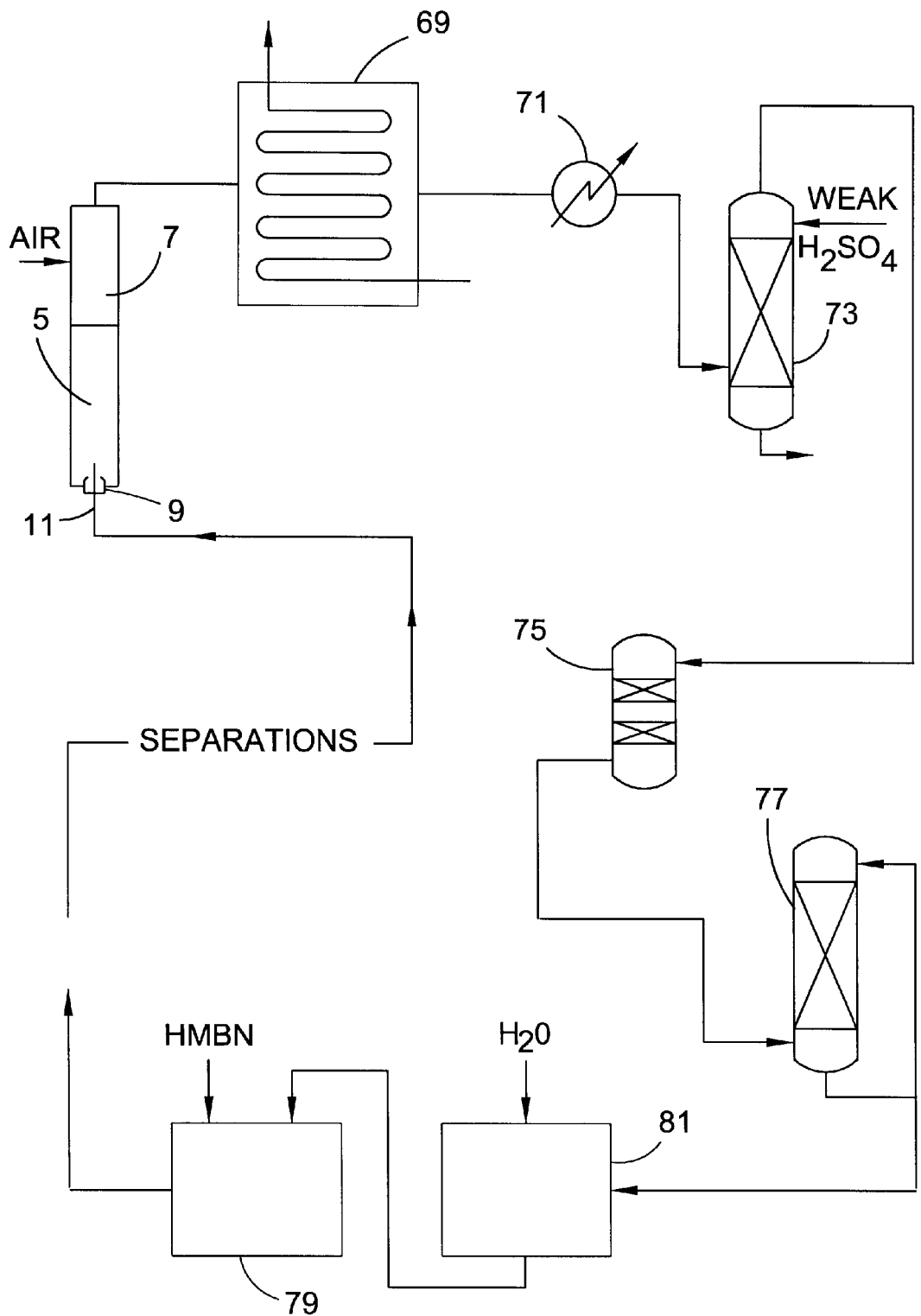
FIG. 5 is a schematic flowsheet illustrating a process for the manufacture of HMBA in which hydrogen sulfide produced by reductive combustion of by-product ammonium bisulfate solution is recovered in the form of regenerated sulfuric acid for recycle to a hydrolysis step for conversion of HMBN to HMBA.

FIG. 5 illustrates the above-noted option of recovering sulfur from the ammonium salt in the form of regenerated sulfuric acid, which may be recycled to the hydrolysis step of a process for the preparation of methionine or HMBA. The drawing specifically depicts a process for the preparation of HMBA, and corresponds directly to the process described in U.S. Pat. No. 5,498,790. In a manner identical or comparable to the process described above with reference to FIG. 4, HMBN is hydrolyzed with sulfuric acid or ammonium bisulfate in a hydrolysis reaction system 79 to produce a hydrolyzate comprising HMBA and by-product ammonium bisulfate and/or ammonium sulfate. An aqueous mixture comprising ammonium bisulfate and/or ammonium sulfate is separated from the hydrolyzate, e.g. by the extraction system of FIG. 4. The aqueous salt mixture is introduced into a reductive combustion zone 5 where it is oxidized to produce a reductive combustion gas having a composition generally as described above. Combustion gas exiting the reductive combustion zone 5 is introduced into a secondary oxidative combustion zone 7 wherein hydrogen sulfide or other divalent sulfur product of the reductive combustion is oxidized to produce sulfur dioxide and water. Carbon monoxide is converted to carbon dioxide. Sufficient secondary air is introduced into the secondary combustion zone for subsequent catalytic oxidation of sulfur dioxide to sulfur trioxide. Alternatively, the $SO_2$ contained in the oxidative combustion gas may be converted to sulfuric acid by reaction with hydrogen peroxide as described in DE 197 54 562 A1. The oxidative combustion gas is cooled in a waste heat boiler 69, optionally further cooled for condensation of water vapor in a condenser 71, and cleaned by countercurrent contact with water or weak sulfuric acid in a scrubbing tower 73. The gas stream containing sulfur dioxide and sulfur trioxide is then introduced into the converter 75 of a contact sulfuric acid plant for conversion of sulfur dioxide to sulfur trioxide over an appropriate catalyst. The sulfur trioxide-bearing stream is contacted with sulfuric acid in an absorber 77 for the production of concentrated acid. The acid may be recycled to the hydrolysis reaction system 79. Since hydrolysis of HMBN requires an acid having a strength in the range of about 55% to about 70% by weight, the typically 98% acid exiting the absorber must be diluted. This can be accomplished in an acid dilution tank 81 as shown in FIG. 5, or by direct introduction of water and sulfuric acid into a continuous hydrolysis reactor as is described in U.S. Pat. No. 5,856,567, also expressly incorporated herein by reference.

Figure 7:
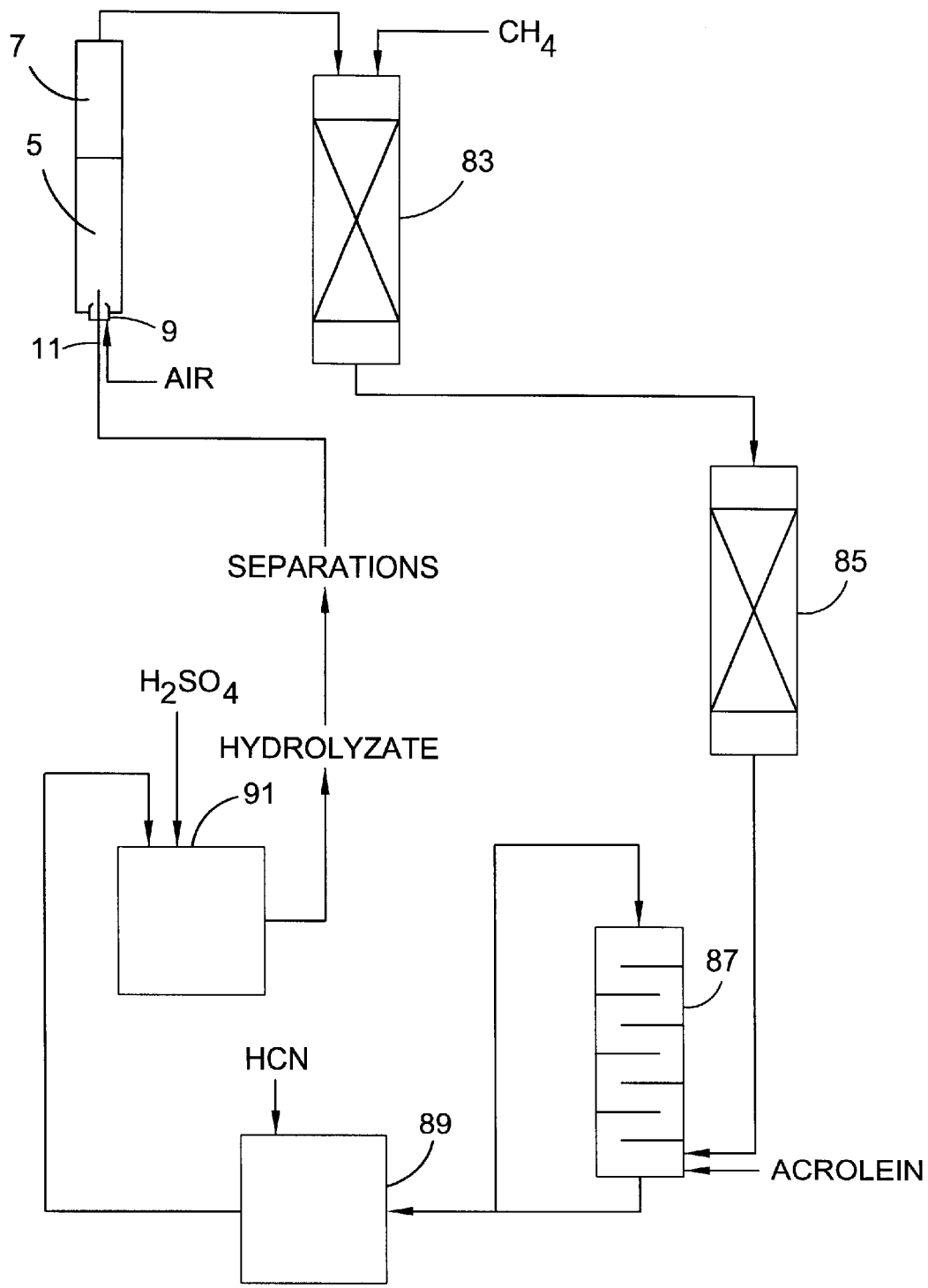
FIG. 7 is a schematic flowsheet illustrating a process for the preparation of HMBA in which $SO_2$ generated in oxidative combustion of by-product ammonium bisulfate solution is reduced by catalytic reaction with methane, and the $H_2S$ produced is converted to methyl mercaptan.

FIG. 7 illustrates a further alternative process for the manufacture of HMBA by hydrolysis of HMBN. By-product aqueous ammonium sulfate or ammonium bisulfate by-product stream is subjected to reductive combustion, producing a combustion gas comprising divalent sulfur compounds. As in the process of FIG. 5, the reductive combustion gas produced in the process of FIG. 7 is subjected to oxidative combustion to produce an oxidative combustion gas comprising sulfur dioxide. However, in the process of FIG. 7, the sulfur dioxide-containing gas stream is not passed over a catalyst for the conversion of sulfur dioxide to sulfur trioxide. Instead sulfur dioxide produced in the oxidative combustion is reduced by reaction with methane, yielding an intermediate reaction gas containing $H_2S$ and carbon oxides which may be used to prepare methyl mercaptan. Prior to catalytic reaction of $SO_2$ with methane, the $SO_2$-bearing secondary combustion gas is preferably concentrated in an absorption/desorption cycle in accordance with the Wellman-Lord process, or using an organic absorbent as described in U.S. Pat. Nos. 3,767,777, 4,530, 204 and 5,851,685, expressly incorporated herein by reference, thereby producing an enriched $SO_2$ which preferably contains at least about 50%, more preferably at least about 90% by volume $SO_2$. The enriched $SO_2$ stream is contacted with a hydrocarbon, preferably methane, over an alumina catalyst in an $SO_2$ reduction reactor 83 at a temperature ranging from about 625° to about 800° C., thereby producing a process gas comprising carbon oxides, hydrogen sulfide and hydrogen. Preferably, the process gas comprises from about 15% to about 50% by volume hydrogen, from about 15% to about 35% by volume hydrogen sulfide, from about 0.3% to about 1% by volume carbonyl sulfide, from about 15% to about 30% by volume carbon monoxide, from about 2.5% to about 20% by volume carbon dioxide, and from about 3.5% to about 15% by volume water vapor. Further details of a process for preparation of $H_2S$ by reduction of $SO_2$ with methane are described in Sarlis and Berk, "Reduction of Sulfur Dioxide with Methane over Activated Alumina", *Ind. Eng. Chem. Res.*, 1988, vol. 27, pp. 1951–1954.

The intermediate reaction gas is suitable for preparation of methyl mercaptan in a reactor 85 that is similar in configuration to catalytic reactor 47 of FIG. 3. Methyl mercaptan is recycled from reactor 85 to an MMP reactor 87 where it is contacted with acrolein in a liquid MMP medium for the preparation of MMP. MMP produced in reactor 87 is contacted with hydrogen cyanide in a reactor 89 to produce HMBN; and HMBN is hydrolyzed with sulfuric acid in reactor 91 for the preparation of HMBA.

Although the processes illustrated in FIGS. 4, 5 and 7 are for the preparation of HMBA, similar processes may be used in the manufacture of methionine. In the preparation of methionine, 2-amino-4-methylthiobutanenitrile rather than HMBN is used as the hydrolysis substrate. The hydroxy nitrile is first prepared by reaction of MMP with HCN in the manner described above, and then converted to the aminonitrile by ammonolysis in a manner well known to the art. Highly conventional processes are also known for the sulfuric acid hydrolysis of 2-amino-4-methylthiobutanenitrile to d,l-methionine, producing an ammonium sulfate by-product solution which can be subjected to reductive combustion in the manner herein described.

In each of the processes of FIGS. 4 and 7, preparation of methyl mercaptan from hydrogen sulfide and carbon monoxide is especially advantageous because the reductive combustion can be controlled in accordance with the invention to produce a combustion gas having significant concentrations of hydrogen sulfide, carbon monoxide, carbonyl sulfide and hydrogen. Depending on the yields realized in the methyl mercaptan reaction, and the material balance of the HMBA process, it may be feasible to obtain methyl mercaptan without introduction of any raw material beyond those otherwise required for the preparation of HMBA. In any event, both sulfur and carbon emissions may be significantly reduced by the recovery of these by-product components in highly useful form. Thus, in the preparation of methyl mercaptan in accordance with the present invention, and especially in the preparation of methyl mercaptan as a precursor for HMBA or methionine, reaction of hydrogen sulfide with carbon monoxide is highly preferred.

However, in various alternative embodiments of the invention, hydrogen sulfide produced in the reductive combustion gas may instead be reacted with methanol in a manner known to the art to produce methyl mercaptan for recycle to the MMP reactor in the process of FIG. 4, the process of FIG. 7, or corresponding processes for the manufacture of d,l-methionine. As described, for example, in EPO patent 0 850 922, expressly incorporated herein by reference, a gas mixture of hydrogen sulfide and methanol may be reacted at a temperature from about 300° to about 500° C. over an aluminum oxide catalyst under an operating pressure ranging from about 5 bar to about 15 bar to yield methyl mercaptan. The aluminum oxide catalyst is preferably coated with a promoter such as an alkali metal tungstate, e.g., potassium or cesium tungstate. The reaction is exothermic and the methanol/hydrogen sulfide feed gas is preferably preheated by transfer of heat from the reaction product gas. The product mixture may contain by-products such as dimethyl sulfide, dimethyl ether, and small quantities of polysulfides, also gases which are inert to the reaction such as nitrogen, carbon dioxide, CO and hydrogen, as well as unreacted methanol and hydrogen sulfide. Methyl mercaptan may be removed from the reaction gas by absorption in an appropriate solvent, preferably methanol, and thereafter refined by distillation. Excess hydrogen sulfide may also be recovered in an absorption/desorption cycle. Unreacted hydrogen sulfide and methanol are recycled to the catalytic reaction zone.

According to a still further alternative, hydrogen sulfide produced in accordance with the reductive combustion process of the invention may be converted to elemental sulfur in a Claus unit. For example, the combustion gas, or a concentrated hydrogen sulfide stream produced in accordance with the process of FIG. 2 hereof, may be contacted with sulfur dioxide, and sulfur produced by the resulting redox reaction according to any of the numerous conventional Claus process schemes well known to the art. Alternatively, hydrogen sulfide may be directly oxidized to elemental sulfur by reaction with oxygen as described in Gowdy et. al, "UOP's Selectox™ Process, Improvements in Technology," Presented at the 48$^{th}$ Annual Laurance Reid Gas Conditioning Conference, Mar. 1–4, 1998, Norman, Okla. Using proprietary Selectox™ catalysts available from UOP, sulfur can be recovered by direct oxidation from streams containing low concentrations of $H_2S$. In the Selectox™ process, direct oxidation produces a reaction mixture in which the predominant sulfur species is elemental sulfur, but which also contains some $SO_2$ and unreacted $H_2S$. The $SO_2$ and $H_2S$ are reacted in a Claus unit downstream of the Selectox™ unit to produce additional elemental sulfur. Optionally, $H_2S$ produced in the reductive combustion gas can be concentrated in an absorption/desorption cycle upstream of the Selectox™ unit. Catalyst life in the Selectox™ process is enhanced by the essentially quantitative destruction of ammonia in the reductive combustion process of the present invention. Catalyst activity and catalyst life are further prolonged by the substantial absence of aromatics from the reductive combustion gas.

Figure 8:
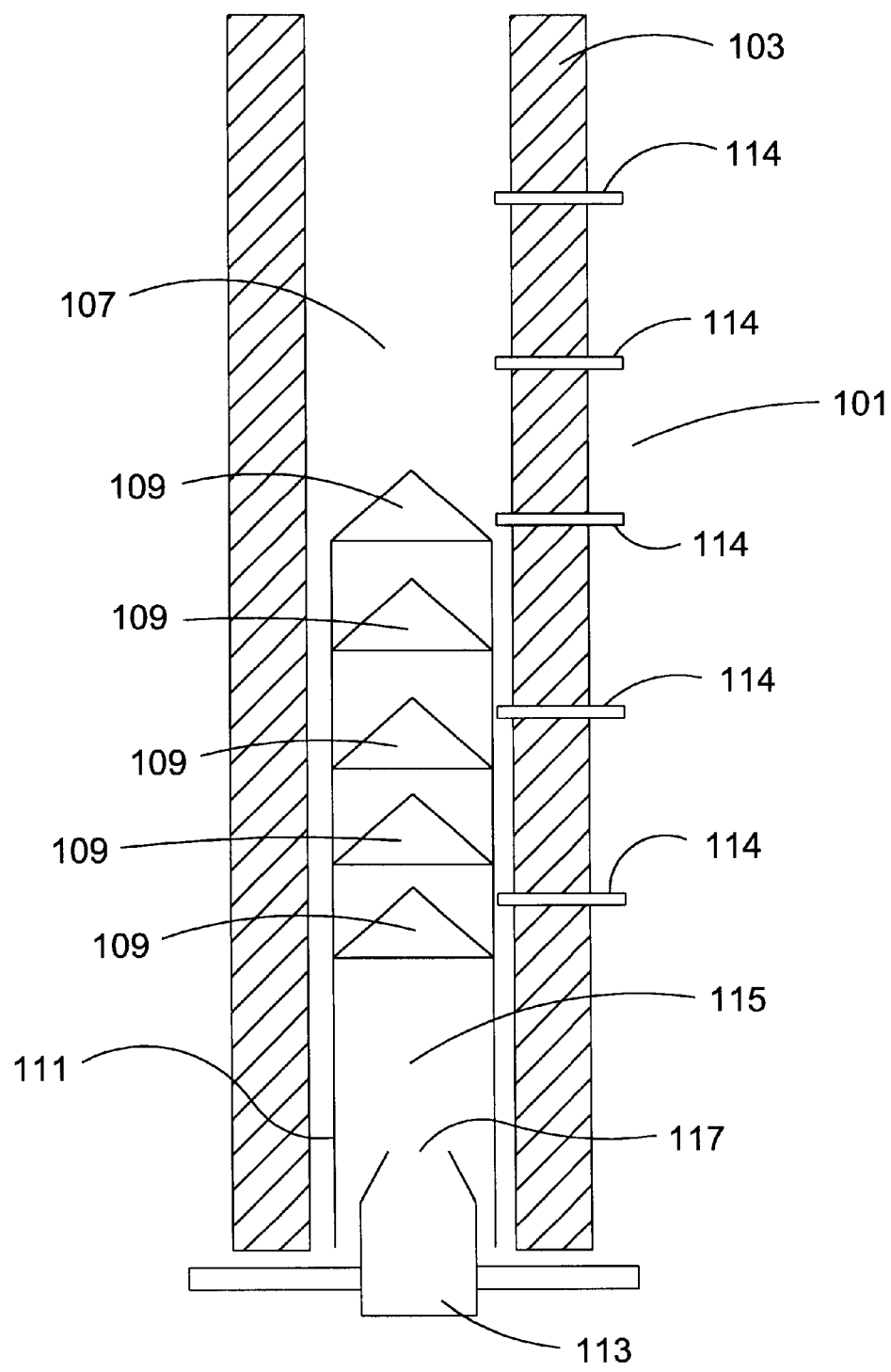
FIG. 8 is a schematic diagram illustrating an apparatus for the reductive combustion of sulfuric acid and/or ammonium salts thereof in which the combustion gas generated in the reductive combustion is contacted with a catalyst in the combustion chamber as described in Example 6.

Illustrated in FIG. 8 is a modification of the apparatus of FIG. 1 effective for the reductive combustion of sulfuric acid and/or ammonium salts thereof in which the gas generated in the reductive combustion is contacted with a catalyst in the combustion chamber. An adiabatic incinerator 101 comprises a vertical cylindrical tube lined with castable refractory 103 comprising either oxides of aluminum or titanium, or alternatively metal sulfides. Inside the incineration chamber, five baffles 109 comprising a ceramic blanket impregnated with either oxides of aluminum or titanium, or alternatively metal sulfides are placed on a stainless steel frame 111. A burner 113 is aligned axially and concentrically of tube 101 in the lower end thereof and oriented for upward discharge of air and fuel, and upward flow of combustion gas through the baffles 109. A quartz jet 117 is positioned for injection of aqueous feed solution upwardly into the reductive combustion zone 115. By modifying the apparatus of FIG. 1 to the configuration of FIG. 8, the combustion gas can be contacted with a catalyst which allows the molar ratio of hydrogen sulfide to carbonyl sulfide in the combustion gas to be at least about 1:1, preferably at least about 4:1, and more preferably at least about 10:1. Contacting the combustion gas with a catalyst also allows the molar ratio of hydrogen sulfide to sulfur dioxide in the combustion gas to be at least about 1.5:1, preferably at least about 10:1, more preferably at least about 40:1 and even more preferably at least about 80:1.

The following examples illustrate the invention.

EXAMPLE 1

Reductive combustion runs were conducted in an apparatus of the type illustrated in FIG. 1. Vertically oriented tubular incinerator 1 comprised a stainless steel pipe with a height of 7 feet (2.13 meters), an internal diameter of 14 inches (35.56 centimeters) and lined with a 3 inch (7.62 centimeter) layer of castable refractory (Kaolite 2300-LI available from Thermal Ceramics of Augusta, Ga.), thus providing a 7 ft.×8 in. (2.13 m×20.32 cm.) diameter combustion reactor. Burner 9 was a nozzle-mixing burner (Eclipse ThermJet 150) having a capacity of 150,000 BTU/hour with a natural gas flow of 35 L/min. The chamber was lined with a series of gas sampling and temperature monitoring ports. The spacing between ports was approximately 30 cm. A 50% by weight solution of ammonium bisulfate was prepared and introduced into reductive combustion zone 5 via a quartz jet 11 having a 6 mm o.d. and a 1 mm i.d.

Air and propane fuel were introduced into burner 9 at rates effective to provide a combustion temperature in the range of about 1200° to about 1400° C. A series of runs were conducted with a stoichiometric deficiency of air. The air supply rate ranged from 37% to 87% of the theoretical rate necessary to supply oxygen in a proportion equivalent to the fuel and ammonium salt introduced into the combustion zone. Residence time in the reductive combustion zone was about 3 to 4 seconds. The combustion gas was sampled with quartz sampling tubes spaced along the length of the chamber. A known volume of combustion gas was pulled through the quartz sampling tube at the desired height above the flame. The samples were drawn with a microprocessor controlled gas sampling pump. Gas samples were introduced into a chromatographic analysis system through fixed (0.1 mL) volume loops. Combustion gas constituents $CO_2$, CO, $O_2$, $H_2O$ and hydrocarbons were analyzed with a gas chromatograph equipped with a thermal conductivity detector (TCD). The gases were separated with a column consisting of an 8 ft.×⅛ in. (2.44 m×0.3175 cm) O.D. stainless steel tube packed with Carbosieve S (100–120 mesh, Supelco Inc., Bellefonte, Pa.). The separated gases were monitored with the TCD.

The concentrations of selected flue gas constituents ($CO_2$, CO, $O_2$, $NO_x$, and $SO_2$) were also determined with an IR based combustion gas analyzer (Bacharach Model 300). The IR analyzer drew samples at a selected flow rate through an absorption cell chamber with a built-in vacuum pump.

(30 mL/min). GC oven temperature was maintained at 100° C. initially, increased to 160° C. at 10° C./min. rate. The $H_2S$ standard was obtained from Matheson Gas Products, PA.

Even 37% theoretical air was found effective to sustain a flame. Compositions of the combustion gases produced in the runs of these examples are set forth in Table 1, together with the waste to fuel ratio, ammonium bisulfate feed concentration and the flame temperature.

A mathematical model was developed to predict the composition of flue gas produced by reductive combustion of ammonium bisulfate solutions of varying concentration at varying theoretical air rates. A digital computer was programmed with this model and combustion gas compositions computed for several of the combinations of conditions under which the above described experimental reductive combustion runs were conducted. The computed combustion gas compositions were then compared to the measured combustion gas compositions for those experimental runs. The model was determined to be generally valid. Using this model, comparative calculations were made of the composition of the combustion gas under certain of the conditions under which experimental runs of this example were conducted. Results of the computer model computations are also set forth in Table 1.

TABLE 1

| | Experimental Results[1,2] | Experimental Results[1,2] | Experimental Results[1,2] | Math Combus Model[1,2] | Experimental Results[1,2] | Math Combust Model[1,2] | Experimental Results[1,2] | Math Combust Model[1,2] | BASF |
|---|---|---|---|---|---|---|---|---|---|
| Fuel | Propane | Propane | Propane | Propane | Propane | Propane | Propane | Propane | Methane |
| ABS Feed Conc. | 50 | 50 | 50 | 50 | 50 | 50 | 50 | 50 | 10% AMS |
| % Theo. Air | 37 | 45 | 65 | 65 | 77 | 77 | 87 | 83 | 80 |
| CO % | 7.8 | 6.8 | 5.2 | 4.4 | 4.0 | 2.6 | 2.3 | 6.5 | 2.8 |
| $CO_2$ % | 10.1 | 10.6 | 12.4 | 12.4 | 13.6 | 13.0 | 14.6 | 4.2 | 10.4 |
| $N_2$ % | 75.1 | 76.6 | 78.6 | 69.3 | 79.2 | 76.7 | 80.8 | 83.4 | 80 |
| $O_2$ % | 0.0 | 0.0 | 0.0 | 0.0 | 0.0 | 0.0 | 0.0 | 0.0 | 0.0 |
| $H_2S$ % | 0.80 | 0.79 | 0.80 | 0.76 | 0.77 | 0.70 | 0.23 | 0.71 | 0.32 |
| COS % | 0.20 | 0.18 | 0.17 | 0.13 | 0.17 | 0.12 | 0.17 | 0.13 | 0.00 |
| $H_2$ % | 5.9 | 5.4 | 3.8 | 13.0 | 3.1 | 6.9 | 2.2 | 0.01 | 6.4 |
| $CH_4$ % | 0.8 | 0.5 | 0.0 | 0.0 | 0.0 | 0.0 | 0.0 | 0.0 | 0.0 |
| $H_2O$ % | | | | ------Dry Gas Percentages------ | | | | | |
| T° C. | 1280° C. | 1227° C. | 1243° C. | | 1260° C. | | 1271° C. | | |

[1]Fuel = 7.9 Liters/min Propane
[2]7.0 moles of ABS salt/m³ of fuel fed to the combustion The concentration of ammonia and sulfur oxides (SOx) was monitored with an ion chromatograph. For these measurements, a known volume of flue gas was passed through a set of deionized water filled impingers. Aliquots from the impinger were injected into the ion chromatograph (Dionex Model 14). Ammonia and SOx were measured as $NH_4^+$ and $SOx^-$ ions. Quantitative analysis of separated ions was carried out with external standards. The cations were separated with a 250×6 mm column (Dionex HPIC-CS 1). A carbonate solution (2.3 mM $NaHCO_3$+1.8 mM $Na_2CO_3$ mixture) was used as the eluant. The anions were separated on a 250×6 mm column (Dionex HPIC-AS3) with 5 mM $HNO_3$ as the eluant.

Quantitative analysis of sulfur-bearing gas species was provided by passing a combustion gas sample through a gas chromatograph equipped with a flame photometric detector (FPD). The GC-FPD permitted quantitative analysis of $H_2S$, COS and $SO_2$. Sulfur-bearing gases were separated with an 8 ft.×⅛ in. (2.44 m×0.3175 cm) O.D. stainless column packed with Porapak (80% Porapak Q and 20% Porapak N, Alltech Associates, Il.). Helium was used as the carrier gas The flame remained stable at all air rates used in the runs of this Example, even upon introduction of 50% ammonium bisulfate solution, which only slightly reduced the flame temperature and only slightly altered the flue gas composition. Measurable amounts of elemental carbon were observed in the flame at theoretical air rates ≦40%. Particulates in the flue gas, primarily constituting elemental carbon and ammonium bisulfate crystals, increased steadily at theoretical air rates below about 65%. However, even at 37% stoichiometric oxygen, the elemental carbon concentration reflected <1% of the carbon content of the propane fuel.

Figure 6:
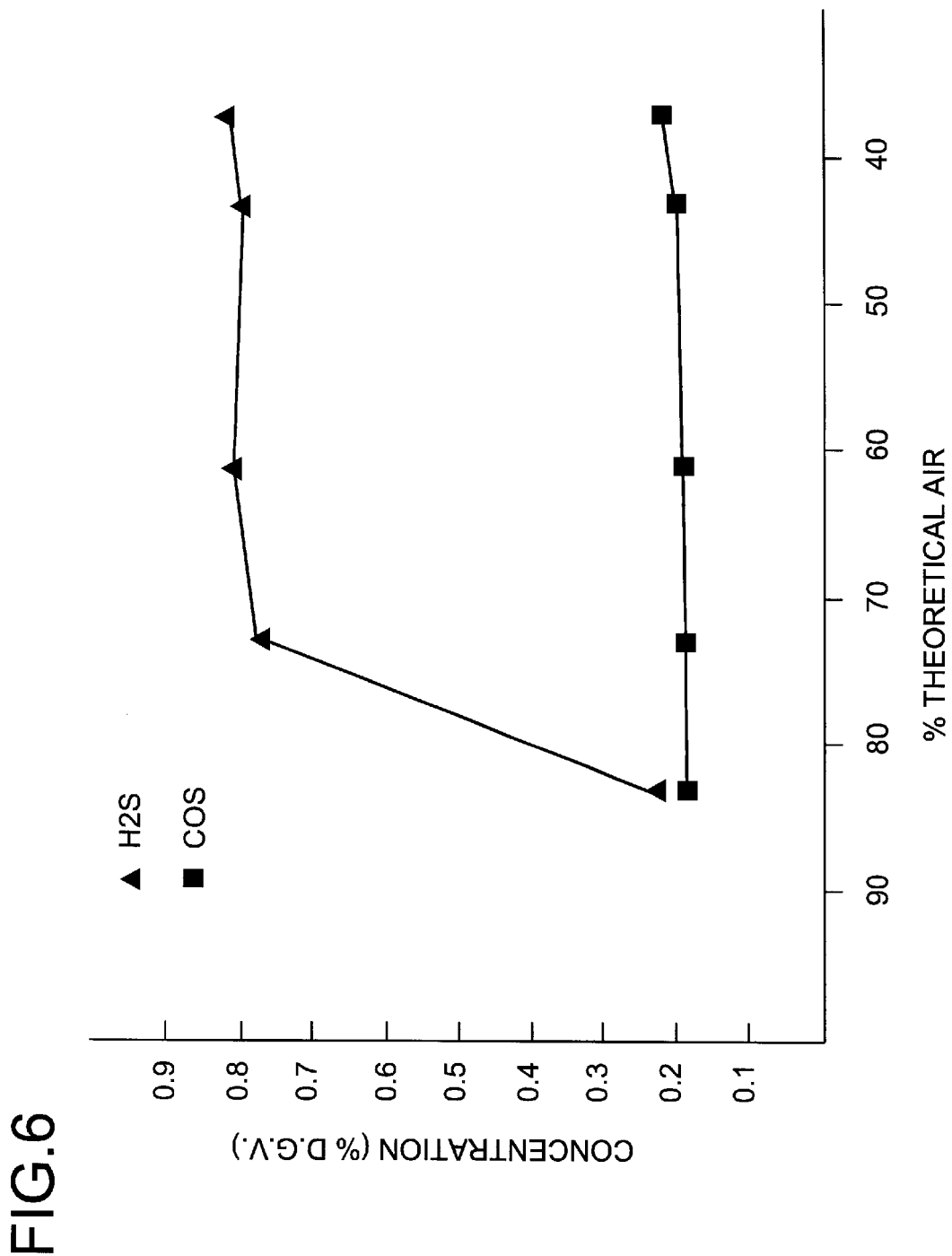
FIG. 6 is a plot of hydrogen sulfide and carbonyl sulfide concentrations (as % dry gas volume) vs. theoretical air in the reductive combustion tests of Example 1.

Hydrogen sulfide concentration was found to be very sensitive to air rate. The hydrogen sulfide concentration was determined to increase gradually with oxygen deficiency to a peak concentration at about 77% theoretical air, and to drop precipitously at theoretical air rates only slightly above 77%. A plot of $H_2S$ and COS concentrations (dry gas volume %) vs. theoretical air for the runs of this example are set forth in FIG. 6. The residual ammonia level from the reductive combustion process were less than 25 ppm by volume.

EXAMPLE 2

Additional reductive combustion runs were conducted in the manner described in Example 1. Comparative calculations were made for runs simulated by the computer model. The concentrations of reduced sulfur species for runs at less than 80% theoretical air showed good agreement with the model. Data at higher than 80% theoretical air showed concentrations of divalent sulfur species that were sharply lower than the concentrations obtained at lower theoretical air rates. Results of these runs are set forth in Table 2. Also included in Table 2 are modeling results for the combustion of 80% by weight ammonium bisulfate solution using conditions of 18.6 gram-moles ammonium bisulfate salt per standard cubic meter fuel.

EXAMPLE 3

A synthetic feed solution for combustion experiments was prepared by dissolving ammonium bisulfate in water at a strength of 50% by weight. A second feed mixture for combustion experiments was provided by taking a sample from the bottom stream exiting the raffinate stripper in a process for the preparation of HMBA generally as described in U.S. Pat. No. 4,524,077. Analysis of the latter sample showed it to contain 51.5% by weight ammonium bisulfate. This sample also contained small amounts of soluble organic components (not analyzed).

Using the apparatus of FIG. 1, the synthetic ammonium bisulfate solution and the raffinate stripper bottoms sample were both subjected to reductive combustion substantially in

TABLE 2

| | Experimental Data | Math. Combust Model | Experimental Data | Math. Combust Model | Experimental Data | Math. Combust Model | Math Combust Model |
|---|---|---|---|---|---|---|---|
| Fuel Type | Propane | Propane | Propane | Propane | Propane | Propane | Propane |
| ABS Feed Conc. | 15 | 15 | 50 | 50 | 50 | 50 | 80 |
| % Theo. Air | 73 | 73 | 73 | 73 | 72 | 72 | 72 |
| Waste/Fuel (moles salt/m³ fuel) | 2.12 | 2.12 | 7.04 | 7.04 | 18.6 | 18.6 | 18.6 |
| CO % | | 3.2 | | 3.2 | | 3.2 | 3.2 |
| $CO_2$ % | | 12.7 | | 12.8 | | 12.8 | 12.8 |
| $N_2$ % | | 73.3 | | 74.4 | | 76.3 | 76.3 |
| $O_2$ % | | 0.0 | | 0.0 | | 0.0 | 0.0 |
| $H_2S$ % | 0.30 | 0.22 | 0.80 | 0.72 | 1.10 | 1.93 | 1.93 |
| $CO_S$ % | 0.04 | 0.04 | 0.16 | 0.13 | 0.26 | 0.34 | 0.34 |
| $H_2$ % | | 10.5 | | 8.8 | | 5.5 | 5.5 |
| $H_2O$ % | | | --------Dry Gas Percentages-------- | | | | |
| $SO_2$ % | | 0.0 | | 0.0 | | 0.0 | 0.0 |
| T° C. | 1380° C. | | 1380° C. | | 1300° C. | | |

The same computer model was used to predict combustion gas compositions obtained in reductive combustion of ammonium bisulfate solutions at varying concentrations, using air enriched with oxygen to a 30% oxygen content as the oxygen containing gas, which was introduced into the combustion zone at rate effective to supply oxygen stoichiometrically equivalent to 73% of the fuel and ammonium bisulfate. Calculations were made for aqueous solutions respectively containing 50%, 85% and 15% by weight ammonium bisulfate. Calculated hydrogen sulfide and carbonyl sulfide concentrations of the combustion gases are set forth in Table 3.

the manner described in Example 1. Conditions of the combustion and analyses of the reductive combustion gases of this example are set forth in Table 4.

TABLE 4

| Aqueous Feed | Synthetic Ammonium Bisulfate[1] | Raffinate Stripper Bottoms[2] |
|---|---|---|
| Fuel Type | Methane | Propane |
| ABS Feed Conc. | 50% | 51.5% |
| % Theoretical Air | 60 | 63 |

TABLE 3

| | Math Combust Model | Math Combust Model | Math Combust Model | Math Combust Model | Math Combust Model | Math Combust Model |
|---|---|---|---|---|---|---|
| Fuel | Propane | Propane | Propane | Propane | Propane | Propane |
| ABS Feed Conc. | 15 | 50 | 80 | 15 | 50 | 80 |
| % Theo. Air | 73 | 73 | 73 | 73 | 73 | 73 |
| Waste Fuel (moles salt/m³ fuel) | 2 | 20 | 20 | 2 | 20 | 20 |
| % $O_2$ in Air Feed | 30 | 30 | 30 | 50 | 50 | 50 |
| CO % | 4.5 | 4.3 | 4.3 | 6.8 | 6.9 | 6.9 |
| $CO_2$ % | 17.7 | 18.0 | 18.0 | 27.7 | 29.0 | 29.0 |
| $N_2$ % | 63.0 | 67.9 | 67.9 | 42.7 | 48.6 | 48.6 |
| $O_2$ % | 0.0 | 0.0 | 0.0 | 0.0 | 0.0 | 0.0 |
| $H_2S$ % | 0.28 | 2.95 | 2.96 | 0.44 | 4.75 | 4.78 |
| COS % | 0.05 | 0.52 | 0.52 | 0.08 | 0.84 | 0.84 |
| $H_2$ % | 14.5 | 6.3 | 6.3 | 22.3 | 9.8 | 9.8 |
| $H_2O$ % | --------Dry Gas Percentages-------- | | | | | |

TABLE 4-continued

| Aqueous Feed | Synthetic Ammonium Bisulfate[1] | Raffinate Stripper Bottoms[2] |
|---|---|---|
| CO % | 3.7 | 4.2 |
| $CO_2$ % | 5.1 | 12.4 |
| $N_2$ % | 88.6 | 78.5 |
| $O_2$ % | 0.6 | 0.0 |
| $H_2S$ % | 0.09 | 0.92 |
| $COS$ % | <0.01 | 0.20 |
| $H_2$ % | 0.2 | 3.6 |
| $CH_4$ % | 1.7 | 0.2 |
| $H_2O$ % | ---- Dry Gas Percentages ---- | |
| T (° C.) | 1200–1300° C. | |

[1]2.9 moles of ABS/STD $m^3$ of fuel, 74 std. liters per minute of air
[2]Approximately 7 moles of ABS Salt/$m^3$ of fuel fed to the combustor

EXAMPLE 4

Comparative

Using an incinerator similar to that of FIG. 1, single stage oxidative combustion experiments were conducted on both the 50% by weight synthetic ammonium bisulfate solution and the raffinate stripper bottom sample described in Example 3. All combustion air was introduced into the combustion zone at the burner. The experiments of this comparative example were conducted at varying proportions of theoretical air. Conditions of the runs of this example and compositions of the oxidative combustion gases produced are set forth in Table 5.

TABLE 5

| | % Excess Air | | | | | | |
|---|---|---|---|---|---|---|---|
| | 100% | 104% | 105% | 107% | 111% | 117% | 118% |
| $NO_x$ (ppm)[1] | | 130 | | | 94 | | 97 |
| T (° C.) | | 1200–1400 | | | 1200–1400 | | 1400–1500 |
| $NO_x$ (ppm)[2] | 102 | 235 | 229 | 250 | 270 | 233 | |
| T (° C.) | 1200–1400 | 1200–1400 | 1200–1400 | 1200–1400 | 1200–1400 | 1200–1400 | |
| $NO_x$ (ppm)[3] | 110 | 305 | 393 | 406 | 436 | 419 | |
| T (° C.) | 1200–1400 | 1200–1400 | 1200–1400 | 1200–1400 | 1200–1400 | 1200–1400 | |

[1]Combustion of Propane Only (7.9 Std Liters/minute propane), average of 3 measurements
[2]Combustion of 50% ABS (7.9 Std Liters/minute fuel; 7.0 moles ABS/Std cubic meter of propane, average of 3 measurements
[3]Combustion of Raffinate Stripper Bottoms (7.9 Std liters/minute propane, 7.25 moles ABS per Std cubic meter of propane, average of 3 measurements)

EXAMPLE 5

Two stage combustion runs were conducted on the 50% ammonium bisulfate synthetic feed solution of Example 3, using the apparatus of FIG. 1. The first stage was run under conditions substantially similar to those described for the reductive combustion runs of Example 1. Secondary air was added to the secondary combustion zone and oxidative combustion was conducted therein. Combustion conditions for the runs of this example and analyses of the oxidative combustion gas produced are set forth in Table 6.

TABLE 6

| | % Theoretical Air Leaving Second Stage | | |
|---|---|---|---|
| $NO_x$ (ppm)[1] | 104 | 109 | 127 |
| T (° C.) | 1200–4400 | 1200–1400 | 1200–1400 |
| $NO_x$ (ppm)[2] | | | |

TABLE 6-continued

| | % Theoretical Air Leaving Second Stage | | |
|---|---|---|---|
| T (° C.) | | | |
| $NO_x$ (ppm)[3] | | | |
| T (° C.) | | | |

[1]Combustion of 50% ABS (7.0 moles ABS/Std. cubic meter of propane, 7.9 Std liters/minute fuel)
[2]Combustion of Novus Raffinate Stripper Bottoms
[3]Combustion of 25% Ammonium Sulfate

EXAMPLE 6

Reductive combustion runs were conducted in an apparatus of the type illustrated in FIG. 8. Vertically oriented tubular incinerator 101 comprised a stainless steel pipe with a height of about 7 feet (2.13 meters), an internal diameter of about 14 inches (35.56 centimeters) and lined with about a 3 inch (7.62 centimeter) layer of castable refractory 103 (Kaolite 2300-LI refractory commercially available from Thermal Ceramics of Augusta, Ga.), thus providing a 6 ft.×8 in. (2.13 m×20.32 cm) diameter combustion reactor 107. The composition of the refractory comprised about 41% alumina ($Al_2O_3$), about 37% silica ($SiO_2$), about 0.9% Ferric oxide ($Fe_2O_3$), about 1.7% titanium oxide ($TiO_2$), about 19% calcium oxide (CaO), about 0.4% magnesium oxide (MgO) and about 0.3% alkalies, e.g., $Na_2O$. Inside the incineration chamber, five baffles 109 of ceramic blanket impregnated with alumina ($Al_2O_3$) were placed on a stainless steel frame 111. Burner 113 was a nozzle-mixing burner (Eclipse ThermJet 150) having a capacity of 158 kJ/hr with a hydrocarbon fuel and air. The chamber was lined with a series of sampling ports (not shown) at 30, 90 and 150 cm above the flame. A 50% by weight solution of ammonium bisulfate was prepared and introduced into reductive combustion zone 115 via a quartz jet 117 having a 6 mm o.d. and a 1 mm i.d. The ammonium bisulfate solution was introduced at a rate of about 6.4 g/min (about 10 ml/min 50% solution).

Propane fuel was introduced into burner 113 at 7.7 liters per minute throughout all of the combustion runs, resulting in an ammonium bisulfate solution feed rate of about 831 mg/L of propane fuel. Combustion runs were conducted at stoichiometric conditions (181.8 LPM of air supplied) as well as with a stoichiometric deficiency of air; 50% stoichiometry (about 92 LPM of air supplied) and 70% stoichiometry (about 127 LPM of air supplied). Residence time in the reductive combustion zone was about 3 to 4 seconds. The combustion gas was sampled with quartz sampling tubes spaced along the length of the chamber. A known volume of combustion gas was pulled through the quartz sampling tube at the desired height above the flame. The samples were drawn with a microprocessor controlled gas sampling pump. Gas samples were introduced into a chromatographic analysis system through fixed (0.1 mL) volume loops. Combustion gas constituents $CO_2$, CO, $O_2$, $H_2O$ and hydrocarbons were analyzed with a gas chromatograph equipped with a thermal conductivity detector (TCD). The gases were separated with a column consisting of an 8 ft.×⅛ in. (2.44 m×0.3175 cm) O.D. stainless steel tube packed with Carbosieve S (100–120 mesh, Supelco Inc., Bellefonte, Pa.). The separated gases were monitored with the TCD.

The concentrations of selected flue gas constituents ($CO_2$, CO, $O_2$, $NO_x$, and $SO_2$) were also determined with an IR based combustion gas analyzer (Bacharach Model 300). The IR analyzer drew samples at a selected flow rate through an absorption cell chamber with a built-in vacuum pump.

Quantitative analysis of sulfur-bearing gas species was provided by passing a combustion gas sample through a gas chromatograph equipped with a flame photometric detector (GC-FPD). The GC-FPD permitted quantitative analysis of $H_2S$, COS and $SO_2$. Sulfur-bearing gases were separated with an 8 ft.×⅛ in. (2.44 m×0.3175 cm) O.D. stainless column packed with Porapak (80% Porapak Q and 20% Porapak N, Alltech Associates, Ill.). Helium was used as the carrier gas (30 mL/min). GC oven temperature was maintained at 100° C. initially, increased to 160° C. at 10° C./min. rate. The $H_2S$ standard was obtained from Matheson Gas Products, PA.

Figure 9B:
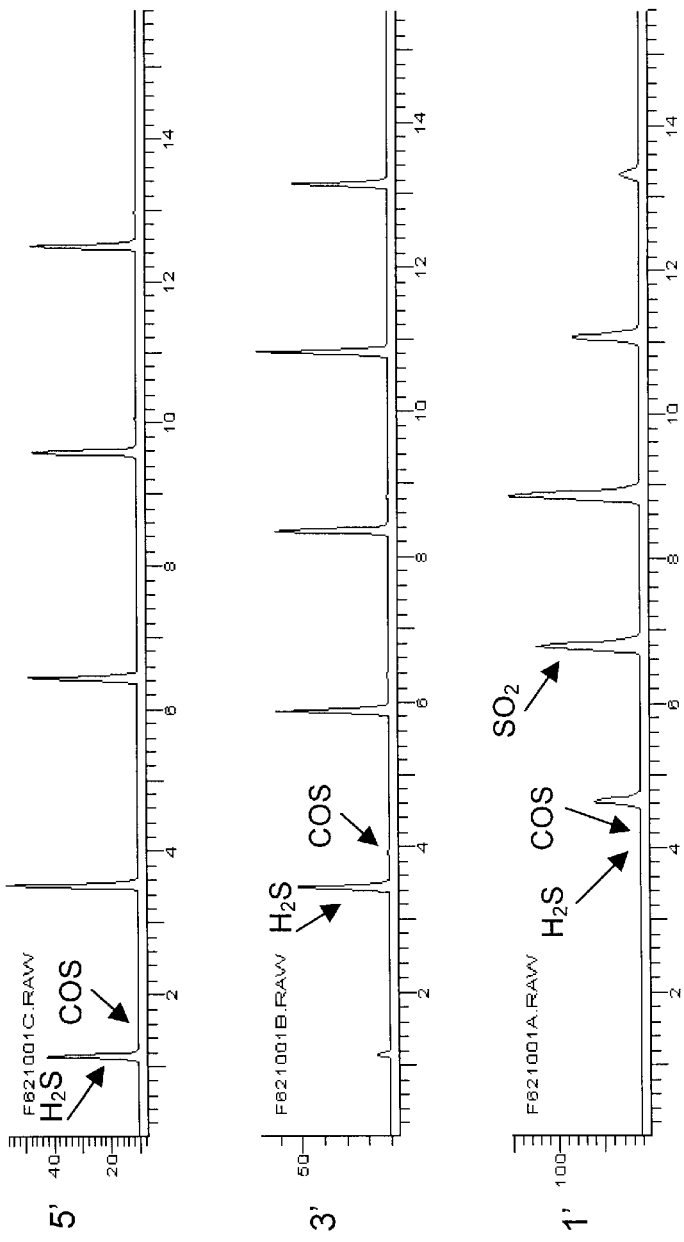
FIG. 9B is a collection of chromatograms showing the sulfur species detected in the combustion gas produced by the 70% stoichiometry combustion runs of Example 6; and, FIG. 10 is a plot of the concentration profiles for sulfur species of the combustion gas produced in the reductive combustion of ammonium bisulfate in Example 6.
Figure 10:
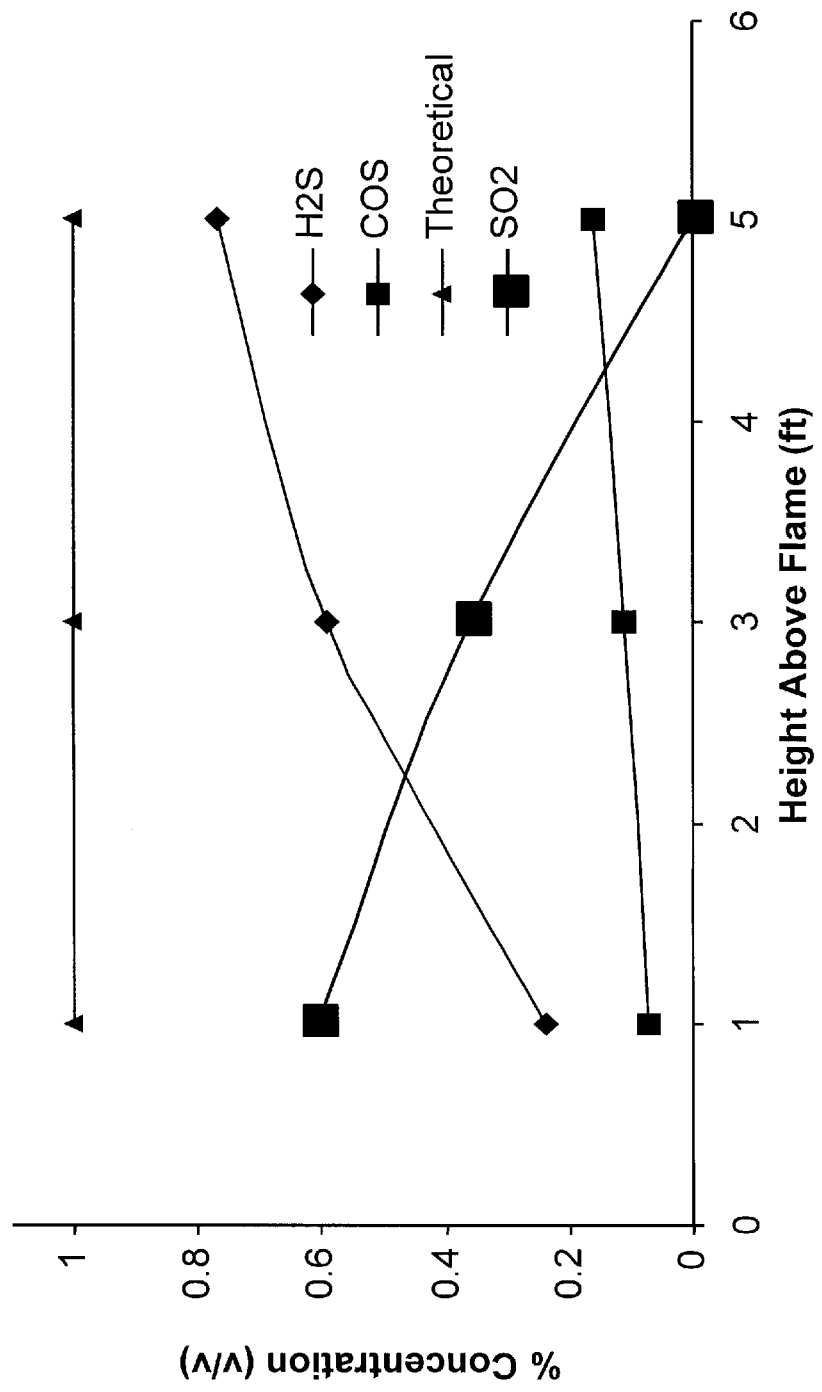

Results from the reductive combustion runs are shown in Tables 7A and 7B with the associated chromatograms from the GC-FPD illustrated in FIGS. 9A and 9B. It should be noted that the actual concentration of $H_2S$ and COS produced is greater than the measured values. The lower measured value results from quenching of $S_2$ emission by residual hydrocarbon (CH4) in the flame photometric detector. FIG. 10 includes a plot showing the measured concentrations of sulfur species at various points along the length of the combustor. $SO_2$ concentration was highest near the flame and decreased further up the chamber. Conversely, the concentrations of $H_2S$ and COS were lowest near the flame and increased away from the flame with near quantitative conversion observed near the exit of the combustion chamber. The maximum concentration of $SO_2$ was observed in samples taken from the 30 cm sampling port when the flame was operating at 70% stoichiometry. Due to turbulent conditions in this region, the measured $SO_2$ values ranged from about 0.56% to about 1.18%. In flue gas samples taken from the 90 and 150 cm sampling ports, $H_2S$ was the only quantifiable sulfur species with a measured concentration of about 0.5 percent. When the flame stoichiometry was reduced to 50% of the theoretical amount of air, the flue gas samples from the 30 cm sampling port contained higher concentrations of COS than the 70% combustion runs. However, $H_2S$ was again the only quantifiable sulfur species in flue gas samples taken from the 90 and 150 cm ports.

TABLE 7A

| Sample Ht (cm) | 30 | 90 | 150 | 30 | 30 | 90 | 30 | 90 | 150 |
|---|---|---|---|---|---|---|---|---|---|
| ABS Feed Conc. | Blank | Blank | Blank | Blank | Blank | Blank | 50 | 50 | 50 |
| % Theo. Air | 100 | 100 | 100 | 70 | 70 | 70 | 70 | 70 | 70 |
| CO % | 0.00 | 0.00 | 0.00 | 5.74 | 4.87 | 3.96 | 4.77 | 4.59 | 4.65 |
| $CO_2$ % | 12.12 | 12.04 | 11.9 | 9.2 | 9.75 | 7.23 | 9.99 | 10.36 | 10.23 |
| $N_2$ % | 86.08 | 85.73 | 85.86 | 80.34 | 80.59 | 80.32 | 80.64 | 80.52 | 80.62 |
| $O_2$ % | 1.80 | 2.24 | 2.24 | 1.00 | 0.99 | 5.68 | 0.90 | 0.79 | 0.92 |
| $CH_4$ % | 0.00 | 0.00 | 0.00 | 0.32 | 0.41 | 0.35 | 0.49 | 0.52 | 0.60 |
| $H_2S$ %[2] | | | | | | | Trace | 0.52 | 0.48 |
| COS % | | | | | | | Trace | Trace | Trace |
| $H_2$ % | 0.00 | 0.00 | 0.00 | 3.41 | 3.38 | 2.46 | 3.21 | 3.22 | 2.97 |
| $SO_2$ % | | | | | | | 0.89[1] | | Trace |
| Flame Temp (° C.) | 1463 | 1485 | 1495 | 1370 | 1170 | 1390 | 1420 | 1179 | 1270 |

[1]Average value, concentrations ranged from 0.56% to 1.18%

TABLE 7B

| Sample Ht (cm) | 30 | 90 | 150 | 30 | 90 | 150 |
|---|---|---|---|---|---|---|
| ABS Feed Conc. | Blank | Blank | Blank | 50 | 50 | 50 |
| % Theo. Air | 50 | 50 | 50 | 50 | 50 | 50 |
| CO % | 7.52 | 8.42 | 8.25 | 7.06 | 6.85 | 6.84 |
| $CO_2$ % | 8.10 | 6.90 | 6.92 | 10.10 | 8.84 | 8.53 |
| $N_2$ % | 69.24 | 76.44 | 76.46 | 75.75 | 77.20 | 77.37 |
| $O_2$ % | 0.81 | 1.12 | 1.10 | 1.02 | 0.90 | 0.92 |
| $CH_4$ % | 1.49 | 1.59 | 1.61 | 1.81 | 1.56 | 1.87 |
| $H_2S$ %[2] | | | | 0.23 | 0.58 | 0.62 |
| COS % | | | | 0.36 | Trace | Trace |
| $H_2$ % | 4.81 | 5.53 | 5.66 | 4.25 | 4.64 | 4.48 |
| $SO_2$ % | | | | | | |
| Flame Temp (° C.) | 942 | 1050 | 992 | 992 | 1224 | 1120 |

[2]The measured $H_2S$ and COS responses have not been corrected by $S_2$ quenching by residual hydrocarbons, thus the results are lower than the calculated values. See the chromatograms of FIGS. 9A and 9B.

What is claimed is:

1. A process for destruction of an aqueous mixture containing an ammonium salt of sulfuric acid, the process comprising introducing an aqueous feed mixture into a reductive combustion zone, said aqueous feed mixture containing ammonium ion in a proportion of at least about 3% by weight and a sulfur-bearing component selected from the group consisting of sulfate ion, bisulfate ion, sulfuric acid, and mixtures thereof in a total proportion of at least about 10% by weight, expressed as $SO_4^{-2}$, thereby producing a combustion gas containing a divalent sulfur compound in a concentration of at least about 4500 ppm by volume, dry gas basis.

2. A process as set forth in claim 1 wherein said divalent sulfur compound is selected from the group consisting of hydrogen sulfide and carbonyl sulfide.

3. A process as set forth in claim 1 wherein said aqueous feed mixture contains at least about 5% by weight ammonium ion and at least about 15% by weight of the sum of sulfate ion, bisulfate ion, sulfuric acid, and mixtures thereof, expressed as $SO_4^{-2}$.

4. A process as set forth in claim 3 wherein said combustion gas contains at least about 5000 ppm volume hydrogen sulfide, dry gas basis.

5. A process as set forth in claim 1 wherein said aqueous feed mixture contains at least 30% by weight ammonium bisulfate.

6. A process as set forth in claim 5 wherein said feed mixture contains at least about 50% by weight ammonium bisulfate.

7. A process as set forth in claim 5 wherein said feed mixture contains at least 20% by weight ammonium sulfate.

8. A process as set forth in claim 1 wherein a fuel, said aqueous feed mixture and an oxygen-containing gas are introduced into said combustion zone in such relative proportions that oxygen is introduced at a rate not greater than about 80% of the theoretical oxygen rate required to oxidize the fuel and other oxidizable components that are introduced into the combustion zone.

9. A process as set forth in claim 8 wherein the rate of introduction of oxygen is not greater than about 75% of the theoretical rate required to oxidize the fuel and other oxidizable components introduced into the combustion zone.

10. A process as set forth in claim 8 wherein the rate of introduction of oxygen is from about 60% to about 75% of the theoretical rate required to oxidize the fuel and other oxidizable components introduced into the combustion zone.

11. A process as set forth in claim 8 wherein said combustion gas contains at least about 5000 ppm by volume hydrogen sulfide and at least about 4% by volume carbon monoxide, dry gas basis.

12. A process as set forth in claim 11 wherein said combustion gas contains at least about 3% by volume hydrogen, dry gas basis.

13. A process as set forth in claim 8 wherein said ammonium salt of sulfuric acid is introduced into said combustion zone in a proportion of at least about 2.5 gram-moles per standard cubic meter of fuel introduced into said combustion zone.

14. A process as set forth in claim 13 wherein said ammonium salt of sulfuric acid is introduced into said combustion zone in a proportion of at least about 5 gram-moles per standard cubic meter fuel introduced into said combustion zone.

15. A process as set forth in claim 8 wherein said fuel comprises a low molecular weight hydrocarbon.

16. A process as set forth in claim 15 wherein said fuel is selected from the group consisting of natural gas, propane, butane and mixtures thereof.

17. A process as set forth in claim 8 wherein the ammonium salt content of said aqueous feed mixture, and the relative rates of introduction of said feed mixture and said fuel are such as to produce at least about 2.5 gram-moles of divalent sulfur compound in said combustion gas per standard cubic meter fuel introduced into said combustion zone.

18. A process as set forth in claim 17 wherein at least about 5 gram-moles of divalent sulfur compound is produced in said combustion gas per standard cubic meter fuel introduced into said combustion zone.

19. A process as set forth in claim 1 wherein the combustion conditions are controlled to produce a combustion gas containing less than about 100 ppm by volume oxides of nitrogen, dry gas basis.

20. A process as set forth in claim 1 wherein the combustion conditions are controlled to produce a combustion gas containing not greater than about 25 ppm by volume ammonia, dry gas basis.

21. A process as set forth in claim 1 wherein the combustion zone temperature is from about 900° to about 1400° C.

22. A process as set forth in claim 1 wherein the divalent sulfur compound comprises hydrogen sulfide and the process further comprises recovery of hydrogen sulfide from the combustion gas.

23. A process as set forth in claim 22 wherein said combustion gas is contacted in an absorption zone with a liquid solvent for hydrogen sulfide, thereby transferring hydrogen sulfide from the gas phase to the solvent phase, and producing a rich absorption liquor containing hydrogen sulfide.

24. A process as set forth in claim 23 wherein hydrogen sulfide is desorbed from the rich absorption liquor in a desorption zone to produce a desorption gas stream containing hydrogen sulfide in a concentration at least about five times the concentration of hydrogen sulfide in said combustion gas and a lean absorption solvent.

25. A process as set forth in claim 1 wherein the combustion gas is contacted with a catalyst effective to promote formation of hydrogen sulfide in the combustion gas.

26. A process as set forth in claim 25 wherein said catalyst is effective to provide a higher ratio of hydrogen sulfide relative to carbonyl sulfide in the combustion gas than the ratio that would prevail in an identical combustion process operated without said catalyst.

27. A process as set forth in claim 26 wherein the molar ratio of hydrogen sulfide to carbonyl sulfide in the combustion gas is at least about 1:1.

28. A process as set forth in claim 26 wherein the molar ratio of hydrogen sulfide to carbonyl sulfide in the combustion gas is at least about 4:1.

29. A process as set forth in claim 26 wherein the molar ratio of hydrogen sulfide to carbonyl sulfide in the combustion gas is at least about 10:1.

30. A process as set forth in claim 25 wherein said catalyst comprises a composition comprising aluminum oxide, or a metal sulfide.

31. A process as set forth in claim 30 wherein said catalyst comprises a metal sulfide selected from the group consisting of FeS, $MoS_2$ and $WS_2$.

32. A process as set forth in claim 25 wherein said catalyst is present in the combustion chamber as a component of a refractory material.

33. A process as set forth in claim 32 wherein said catalyst comprises a mixed metal oxide comprising an oxide of aluminum.

34. A process as set forth in claim 25 wherein said combustion gas is contacted with said catalyst in a catalytic conversion zone.

35. A process as set forth in claim 34 wherein said combustion zone comprises said catalytic conversion zone.

36. A process as set forth in claim 34 wherein said combustion zone and said catalytic conversion zone are substantially coextensive.

37. A process as set forth in claim 34 wherein the exit of said catalytic conversion zone is downstream of said combustion zone with respect to the flow of combustion gas.

38. A process as set forth in claim 34 wherein the inlet of said catalytic conversion zone is downstream of said combustion zone with respect to the flow of combustion gas.

39. A process as set forth in claim 1 wherein the combustion gas is contacted with a catalyst effective to promote the conversion of sulfur dioxide to hydrogen sulfide in the combustion gas.

40. A process as set forth in claim 39 wherein the molar ratio of hydrogen sulfide to sulfur dioxide in the combustion gas is at least about 1.5:1.

41. A process as set forth in claim 40 wherein the molar ratio of hydrogen sulfide to sulfur dioxide in the combustion gas is at least about 10:1.

42. A process as set forth in claim 41 wherein the molar ratio of hydrogen sulfide to sulfur dioxide in the combustion gas is at least about 40:1.

* * * * *